US009111345B2

(12) United States Patent
Sato et al.

(10) Patent No.: US 9,111,345 B2
(45) Date of Patent: Aug. 18, 2015

(54) MEDICAL IMAGE COMPRESSION DEVICE, MEDICAL IMAGE COMPRESSION METHOD, AND PREDICTION KNOWLEDGE DATABASE CREATION DEVICE

(71) Applicant: Panasonic Corporation, Osaka (JP)

(72) Inventors: Yoshikuni Sato, Fukui (JP); Hideto Motomura, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 104 days.

(21) Appl. No.: 14/086,262

(22) Filed: Nov. 21, 2013

(65) Prior Publication Data

US 2014/0079302 A1    Mar. 20, 2014

Related U.S. Application Data

(63) Continuation of application No. PCT/JP2012/007223, filed on Nov. 12, 2012.

(30) Foreign Application Priority Data

Nov. 25, 2011    (JP) .................................. 2011-257887

(51) Int. Cl.
*G06K 9/00* (2006.01)
*G06K 9/36* (2006.01)
(Continued)

(52) U.S. Cl.
CPC .............. *G06T 9/004* (2013.01); *G06T 7/0012* (2013.01); *H04N 19/593* (2014.11); *H04N 19/63* (2014.11); *H04N 19/91* (2014.11); *A61B 6/032* (2013.01); *A61B 6/52* (2013.01)

(58) Field of Classification Search
None
See application file for complete search history.

(56) References Cited

U.S. PATENT DOCUMENTS 6,081,612 A * 6/2000 Gutkowicz-Krusin
et al. .............................. 382/128
7,031,506 B2 * 4/2006 Tsujii et al. ................... 382/132
(Continued)

FOREIGN PATENT DOCUMENTS

JP    6-284294    10/1994
JP    9-168149    6/1997
(Continued)

OTHER PUBLICATIONS

Gokturk, Salih B., et al. "Medical image compression based on region of interest, with application to colon CT images." Engineering in Medicine and Biology Society, 2001. Proceedings of the 23rd Annual International Conference of the IEEE. vol. 3. IEEE, 2001.*
(Continued)

*Primary Examiner* — Stephen R Koziol
*Assistant Examiner* — Sean Conner
(74) *Attorney, Agent, or Firm* — Wenderoth, Lind & Ponack, L.L.P.

(57) ABSTRACT

A medical image compression device includes: a compression target obtaining unit obtaining a target medical image to be compressed and diagnostic finding information for the target image; a clinical condition range obtaining unit dividing the target image into regions for the respective clinical conditions based on the diagnostic finding information; a pixel value prediction unit, for an arbitrary pixel, referring to a prediction knowledge database, and calculating a prediction probability of a value of a prediction target pixel based on the clinical condition of the prediction target pixel and the appearance distribution of the value of the prediction target pixel; a coding unit coding the value of the prediction target pixel based on the prediction probability of the pixel value; and an output unit outputting a code of the prediction target pixel after being coded by the coding unit.

11 Claims, 20 Drawing Sheets

(51) Int. Cl.
*G06T 9/00* (2006.01)
*G06T 7/00* (2006.01)
*H04N 19/63* (2014.01)
*H04N 19/593* (2014.01)
*H04N 19/91* (2014.01)
*A61B 6/03* (2006.01)
*A61B 6/00* (2006.01)

(56) References Cited

U.S. PATENT DOCUMENTS

| | | | | |
|---|---|---|---|---|
| 7,587,073 | B2 * | 9/2009 | Park | 382/128 |
| 7,676,102 | B2 | 3/2010 | Sakai et al. | |
| 8,311,962 | B2 * | 11/2012 | Kato et al. | 706/20 |
| 8,787,634 | B2 * | 7/2014 | Wiemker et al. | 382/128 |
| 2007/0236491 | A1 * | 10/2007 | Hundley et al. | 345/418 |
| 2007/0248271 | A1 * | 10/2007 | Sakai et al. | 382/236 |
| 2008/0118123 | A1 * | 5/2008 | Ogura et al. | 382/128 |
| 2008/0139920 | A1 * | 6/2008 | Biglieri et al. | 600/410 |
| 2013/0301889 | A1 * | 11/2013 | Abramoff et al. | 382/128 |
| 2014/0072193 | A1 * | 3/2014 | Motomura et al. | 382/128 |
| 2014/0119624 | A1 * | 5/2014 | Ehlers et al. | 382/131 |

FOREIGN PATENT DOCUMENTS

| | | |
|---|---|---|
| JP | 2007-295170 | 11/2007 |
| WO | 2008/139825 | 11/2008 |

OTHER PUBLICATIONS

Poggi, Giovanni, and Richard A. Olshen. "Pruned tree-structured vector quantization of medical images with segmentation and improved prediction." Image Processing, IEEE Transactions on 4.6 (1995): 734-742.*

Qi, Xiaojun, and John M. Tyler. "A progressive transmission capable diagnostically lossless compression scheme for 3D medical image sets." Information Sciences 175.3 (2005): 217-243.*

International Search Report issued in International Application PCT/JP2012/007223 on Jan. 15, 2013.

* cited by examiner

FIG. 5

> Early stain is observed in Liver S3 segment. In late phase, low absorption is indicated, and thus Hepatocellular carcinoma is considered. There is cyst in Liver S5.

FIG. 6

| Position | Clinical condition |
|---|---|
| Liver S3 | Hepatocellular carcinoma |
| Liver S5 | Cyst |

FIG. 7

| Position | Clinical condition |
|---|---|
| Liver S3 | Early stain |
| Liver S3 | Washout |
| Liver S3 | Hepatocellular carcinoma |
| Liver S5 | Cyst |

FIG. 8

| Time phase | Position | Clinical condition |
|---|---|---|
| Early phase | Liver S3 | Early stain |
| Late phase | Liver S3 | Washout |
| Entirety | Liver S3 | Hepatocellular carcinoma |
| Entirety | Liver S5 | Cyst |

| Position KW | Region |
|---|---|
| Right hepatic lobe | (100, 100) - (200, 400) |
| Left hepatic lobe | (200, 100) - (350, 150) |
| Liver S1 | (300, 300) - (350, 350) |
| Liver S2 | (250, 300) - (300, 350) |
| Liver S3 | (100, 100) - (150, 150) |
| ... | ... |

| Position KW | Region |
|---|---|
| Right hepatic lobe | (110, 115), (110, 115), (109, 116), (110, 116), ··· |
| Left hepatic lobe | (225, 118), (226, 118), (227, 118), (220, 119), ··· |
| Liver S1 | (340, 305), (333, 306), (334, 306), (335, 336), ··· |
| Liver S2 | (260, 310), (261, 310), (262, 310), (263, 310), ··· |
| Liver S3 | (120, 120), (121, 120), (122, 120), (123, 120), ··· |
| ··· | ··· |

| Region | Clinical condition |
|---|---|
| (100, 100) - (200, 200) | Hepatocellular carcinoma |
| (250, 400) - (350, 450) | Cyst |

FIG. 14

| 75 | 80 | 72 | 66 | 77 | 68 | 68 | 64 |
|----|----|----|----|----|----|----|----|
| 66 | 72 | 72 | 65 | 70 | 67 | 71 | 69 |
| 59 | 65 | 66 | 64 | 72 | 73 | 66 | 70 |
| 61 | 68 | 68 | 65 | 70 | 71 | 69 | 74 |
| 72 | 70 | 69 | 67 | 72 | 68 | 71 | 74 |
| 70 | 71 | 67 | 69 | 70 | 66 | 69 | 70 |
| 60 | 60 | 62 | 61 | 60 | 55 | 61 | 64 |
| 55 | 58 | 61 | 58 | 59 | 58 | 58 | X  |

FIG. 15

[Range Example of neighboring pixel pattern of portion a]

| 50 | 55 |
|----|----|
| 53 | a  |

[Range Example of neighboring pixel pattern of portion b]

| 25 | 11 |    |
|----|----|----|
|    | 75 | 60 |
|    | 62 | b  |

FIG. 18

| Row number | Clinical condition | Threshold | Neighboring pixel | | | | | | | | | Appearance distribution of prediction target pixel | | | | | | | | |
|---|---|---|---|---|---|---|---|---|---|---|---|---|---|---|---|---|---|---|---|---|
| | | | A | B | C | D | E | F | G | H | ... | 0 | 1 | ... | 59 | 60 | 61 | ... | 254 | 255 |
| 1 | Hepatocellular carcinoma | 5 | 64 | 61 | 58 | 10 | 8 | -5 | 5 | 5 | ... | 0 | 0 | ... | 48 | 58 | 53 | ... | 0 | 0 |
| 2 | Hepatocellular carcinoma | 5 | 60 | 55 | 58 | 7 | -6 | / | / | / | ... | 0 | 0 | ... | 60 | 48 | 24 | ... | 0 | 0 |
| 3 | Hepatocellular carcinoma | 5 | 90 | 91 | 90 | 6 | 5 | -6 | / | 5 | ... | 0 | 0 | ... | 0 | 3 | 5 | ... | 1 | 0 |
| ... | ... | ... | | | | | | | | | ... | | | ... | | | | ... | | |
| 101 | Cyst | 5 | 60 | 55 | 58 | 7 | -6 | / | / | / | ... | 1 | 1 | ... | 35 | 24 | 16 | ... | 0 | 0 |
| 102 | Cyst | 5 | 50 | 54 | 51 | 8 | / | / | / | / | ... | 0 | 0 | ... | 10 | 4 | 1 | ... | 2 | 1 |
| 103 | Cyst | 5 | 54 | 61 | 59 | / | / | / | / | / | ... | 0 | 0 | ... | 8 | 6 | 5 | ... | 2 | 0 |
| ... | ... | ... | | | | | | | | | ... | | | ... | | | | ... | | |

FIG. 21
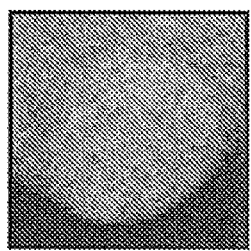
1. Hepatocellular carcinoma
2. Angioma
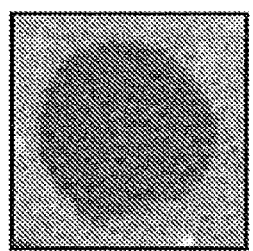
3. Cyst

FIG. 22

| Row number | Clinical condition | Threshold | Neighboring pixel ||||||||| Appearance distribution of prediction target pixel |||||||||
|---|---|---|---|---|---|---|---|---|---|---|---|---|---|---|---|---|---|---|
| | | | A | B | C | D | E | F | G | H | 0 | 1 | ... | 59 | 60 | 61 | ... | 254 | 255 |
| 1 | Hepatocellular carcinoma | 5 | 64 | 61 | 58 | 10 | -8 | -5 | 5 | 5 | ... | 0 | 1 | ... | 48 | 59 | 53 | ... | 0 | 0 |
| 2 | Hepatocellular carcinoma | 5 | 60 | 55 | 58 | 7 | -6 | -5 | / | / | ... | 0 | 0 | ... | 60 | 48 | 24 | ... | 0 | 0 |
| 3 | Hepatocellular carcinoma | 5 | 90 | 91 | 90 | 6 | 5 | -6 | / | 5 | ... | 0 | 0 | ... | 0 | 3 | 5 | ... | 1 | 0 |
| ... | ... | ... | | | | | | | | | ... | | | ... | | | | ... | | |
| 101 | Cyst | 5 | 60 | 55 | 58 | 7 | -6 | / | / | / | ... | 1 | 1 | ... | 35 | 24 | 16 | ... | 0 | 0 |
| 102 | Cyst | 5 | 50 | 54 | 51 | 8 | / | / | / | / | ... | 0 | 0 | ... | 10 | 4 | 1 | ... | 2 | 1 |
| 103 | Cyst | 5 | 54 | 61 | 59 | / | / | / | / | / | ... | 0 | 0 | ... | 8 | 6 | 5 | ... | 2 | 0 |
| ... | ... | ... | | | | | | | | | ... | | | ... | | | | ... | | |

FIG. 23

| Row number | Clinical condition | Threshold | Neighboring pixel | | | | | | | | | Appearance distribution of prediction target pixel | | | | | | | |
|---|---|---|---|---|---|---|---|---|---|---|---|---|---|---|---|---|---|---|---|
| | | | A | B | C | D | E | F | G | H | ... | 0 | 1 | ... | 59 | 60 | 61 | ... | 254 | 255 |
| 1 | Hepatocellular carcinoma | 5 | 64 | 61 | 58 | 10 | 8 | -5 | 5 | 5 | ... | 0 | 1 | ... | 48 | 59 | 53 | ... | 0 | 0 |
| 2 | Hepatocellular carcinoma | 5 | 60 | 55 | 58 | 7 | -6 | -5 | / | / | ... | 0 | 0 | ... | 60 | 48 | 24 | ... | 0 | 0 |
| 3 | Hepatocellular carcinoma | 5 | 90 | 91 | 90 | 6 | 5 | -6 | / | 5 | ... | 0 | 0 | ... | 0 | 3 | 5 | ... | 1 | 0 |
| ... | ... | ... | | | | | | | | | ... | | | ... | | | | ... | | |
| 101 | Cyst | 5 | 60 | 55 | 58 | 7 | -6 | / | / | / | ... | 1 | 1 | ... | 35 | 24 | 16 | ... | 0 | 0 |
| 102 | Cyst | 5 | 50 | 54 | 51 | 8 | / | / | / | / | ... | 0 | 0 | ... | 10 | 4 | 1 | ... | 2 | 1 |
| 103 | Cyst | 5 | 54 | 61 | 59 | / | / | / | / | / | ... | 0 | 0 | ... | 8 | 6 | 5 | ... | 2 | 0 |
| 104 | Cyst | 5 | 60 | 61 | 60 | 5 | / | / | / | / | ... | 0 | 0 | ... | 1 | 0 | 0 | ... | 0 | 0 |
| ... | ... | ... | | | | | | | | | ... | | | ... | | | | ... | | |

| Pixel value | Normal expression (8bit) | Prediction probability | Huffman coding |
|---|---|---|---|
| 0 | 00000000 | 0.01 | 111111111110 |
| 1 | 00000001 | 0.01 | 1111111111110 |
| ... | ... | ... | ... |
| 59 | 00111011 | 0.25 | 00 |
| 60 | 00111100 | 0.25 | 01 |
| 61 | 00111101 | 0.15 | 101 |
| ... | ... | ... | ... |
| 254 | 11111110 | 0.01 | 11111111111110 |
| 255 | 11111111 | 0.01 | 11111111111111 |

FIG. 27

| Clinical condition | Threshold |
|---|---|
| Hepatocellular carcinoma | 5 |
| Liver cyst | 3 |
| Angioma | 10 |
| ... | ... |

MEDICAL IMAGE COMPRESSION DEVICE, MEDICAL IMAGE COMPRESSION METHOD, AND PREDICTION KNOWLEDGE DATABASE CREATION DEVICE

CROSS REFERENCE TO RELATED APPLICATIONS

This is a continuation application of PCT International Application No. PCT/JP2012/007223 filed on Nov. 12, 2012, designating the United States of America, which is based on and claims priority of Japanese Patent Application No. 2011-257887 filed on Nov. 25, 2011. The entire disclosures of the above-identified applications, including the specifications, drawings and claims are incorporated herein by reference in their entirety.

FIELD

One or more exemplary embodiments disclosed herein relate to a medical image compression device and a medical image compression method which are used for compressing an image for medical use (a medical image) with high compression efficiency and a prediction knowledge database creation device for creating a prediction knowledge database for use in the medical image compression device.

BACKGROUND

Recent development and widespread use of medical image devices for computed tomography (CT) and magnetic resonance imaging (MRI) have made it possible to obtain a large volume of high-definition digital images for medical use. Such medical images are accumulated in picture archiving and communication systems (PSCS), together with findings (report) obtained when a doctor examines an image for diagnosis. The amount of medical images which can be acquired has increased more and more with the enhanced performance of devices, and thus a medical image compression technique which allows high compression is in high demand. In addition, a high image quality is required for medical images, and thus generally lossless image compression is carried out. General compression techniques such as JPEG-LS, Lossless JPEG, and JPEG2000 are used in current medical image compression. In recent years, in addition to these technical backgrounds, images of tissues or cells along with radiological images are also stored increasingly as virtual slides. These images have larger volume compared to the radiological images, and thus a demand for medical image compression is likely to increase more and more in the future.

Patent Literature (PTL) 1 discloses a conventional technique related to the lossless medical image compression. PLT 1 focuses on the point that medical images have larger noises compared to natural images, and presents a solution for that. In particular, in the case of image capturing using multi-slice CT, radial noise (artifact) is likely to be generated, leading to decrease in the compression efficiency. PLT 1 solves such a problem by dividing an image into regions and performing compression for each corresponding region, improving the compression efficiency in conventional lossless compression on medical images.

CITATION LIST

Patent Literature

[PLT 1] Japanese Unexamined Patent Application Publication No. 2007-295170

SUMMARY

Technical Problem

However, with the conventional configuration described above, the region division is carried out not based on a medical structure, and thus the region division carried out is not necessarily suitable to the compression. Furthermore, although neighboring pixels for use in predicting a pixel value based on the neighboring pixels are weighted according to the degree of importance, what range of neighboring pixels are to be used is not taken into consideration. For that reason, there is a problem that medical images cannot be compressed with high compression efficiency.

The present disclosure has been conceived to solve the above-described problem, and one non-limiting and exemplary embodiment provides a medical image compression device capable of compressing medical images with high compression efficiency in a lossless scheme.

Solution to Problem

In one general aspect, the techniques disclosed here feature a medical image compression device including: a compression target obtaining unit configured to obtain (i) a target image which is a medical image to be compressed and (ii) diagnostic finding information for the target image; a clinical condition range obtaining unit configured to divide the target image into regions each corresponding to a different one of clinical conditions based on the diagnostic finding information; a pixel value prediction unit configured to, for an arbitrary pixel, refer to a prediction knowledge database in which an appearance distribution of a pixel value of an arbitrary pixel is stored for each of the clinical conditions, and calculate a prediction probability of a pixel value of a prediction target pixel based on the clinical condition of the prediction target pixel and the appearance distribution of the pixel value of the prediction target pixel, the appearance distribution of the pixel value of the arbitrary pixel corresponding to a pixel value included in a predetermined neighboring range; a coding unit configured to code the pixel value of the prediction target pixel based on the prediction probability of the pixel value calculated by the pixel value prediction unit; and an output unit configured to output a code of the prediction target pixel after being coded by the coding unit.

According to this configuration, the medical image compression device divides, by utilizing diagnostic finding information, a target image into regions each of which corresponds to a different one of clinical conditions. In addition, by predicting a pixel value of a prediction target pixel with use of, as knowledge, an appearance distribution of a pixel value which corresponds to (i) the clinical condition obtained from a past case and (ii) a pixel value of a pixel included in a neighboring range, it is possible to predict a pixel value suitable to an image (a medical image, in this case) of a target for compression. For that reason, it is possible to compress a medical image with high compression efficiency and a lossless scheme.

A prediction knowledge database creation device according to another aspect of the present disclosure is a prediction knowledge database which creates a prediction knowledge database for use in the medical image compression device described above, the prediction knowledge database creation device including: a case selecting unit which selects a nonselected case from a case database as a result of an examination for diagnosis of the medical image by a doctor, the case database holding a plurality of cases each including a medical image and diagnostic finding information which includes at least a clinical condition and information related to a position of the clinical condition; a finding analyzing unit which refers to a medical dictionary in which (i) a clinical condition keyword which is a term indicating a clinical condition and (ii) a position keyword which is a term indicating a position of the clinical condition are held, and extracts the clinical condition keyword and the position keyword from the diagnostic finding information included in the case selected by the case selecting unit; the clinical condition range obtaining unit which refers to an anatomical structure database in which the position keyword and range information of a clinical condition on a medical image are held in association with each other, and obtains range information of a clinical condition on the medical image, which corresponds to the position keyword extracted by the finding analyzing unit and included in the case selected by the case selecting unit; an image frequency analyzing unit which performs frequency analysis on the medical image included in the case selected by the case selecting unit; a neighboring pixel pattern generating unit which generates a neighboring pixel pattern including pixel values of pixels included in a predetermined range which includes neighboring pixels of a target pixel, in the medical image on which the frequency analysis has been performed by the image frequency analyzing unit, and a pixel value frequency distribution updating unit which obtains, from the prediction knowledge database, row data corresponding to the clinical condition keyword extracted by the finding analyzing unit and the neighboring pixel pattern generated by the neighboring pixel pattern generating unit, and updates, using the pixel value of the target pixel, an appearance distribution of a pixel value of an arbitrary pixel included in the obtained row data.

According to this configuration, the prediction knowledge database creation device obtains, with use of the diagnostic finding information, a clinical condition and information on a range of the clinical condition. In addition, the prediction knowledge database creation device generates a pattern (neighboring pixel pattern) of pixel values in a neighboring pixel region, which is to be used for predicting a pixel value from an image on which frequency analysis has been performed. In addition, it is possible to construct a prediction knowledge database which utilizes, as knowledge, an appearance distribution of an actual pixel value, which corresponds to the clinical condition obtained from a past case and a neighboring pixel pattern. By predicting a pixel value of a prediction target pixel using such a prediction knowledge database, it is possible to predict a pixel value suitable to an image (a medical image, in this case) of a target for compression. For that reason, it is possible to compress a medical image with high compression efficiency and a lossless scheme.

It is to be noted that these generic and specific aspects may be implemented using a system, a method, an integrated circuit, a computer program, or a non-transitory computer-readable recording medium such as a compact disc read only memory (CD-ROM), and may also be implemented by any combination of systems, apparatuses, methods, integrated circuits, computer programs, and recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

One or more exemplary embodiments or features disclosed herein enable compressing a medical image with high compression efficiency and in a lossless scheme.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 5 is a diagram illustrating an example of diagnostic finding information obtained by an abdominal CT scan according to Embodiment 1.

FIG. 6 is a diagram illustrating the case where a position keyword and a clinical condition keyword are obtained as a set from the diagnostic finding information, according to Embodiment 1.

FIG. 7 is a diagram illustrating the case where a disease name and a term indicating how a clinical condition looks on the image are obtained as clinical condition keywords, according to Embodiment 1.

FIG. 8 is a diagram illustrating the case where information on a time phase is extracted from the diagnostic finding information, in addition to the position keyword and the clinical condition keyword, according to Embodiment 1.

FIG. 14 is a diagram illustrating an example of neighboring pixels of a pixel X which is a target of prediction, according to Embodiment 1.

FIG. 15 is a diagram illustrating the case where image frequency analysis (wavelet transformation) is performed, according to Embodiment 1.

FIG. 18 is a diagram illustrating a structure of the prediction knowledge database according to Embodiment 1.

FIG. 21 is a diagram illustrating an example of three types of liver tumors (hepatocyte cancer, angioma, and cyst) in an abdominal contrast enhanced CT image (arterial phase), according to Embodiment 1.

FIG. 22 is a diagram illustrating the case where an appearance distribution of pixel values is updated (in the case where the same clinical conditions and the same patterns of neighboring pixels are present in the appearance distribution of pixel values), according to Embodiment 1.

FIG. 23 is a diagram illustrating the case where an appearance distribution of pixel values is updated (in the case where the same clinical conditions and the same patterns of neighboring pixels are not present in the appearance distribution of pixel values).

FIG. 27 is a diagram illustrating an example of storage format of a threshold in the prediction knowledge database when using a different threshold for each clinical condition, according to Embodiment 2.

DESCRIPTION OF EMBODIMENTS

Figure 1:
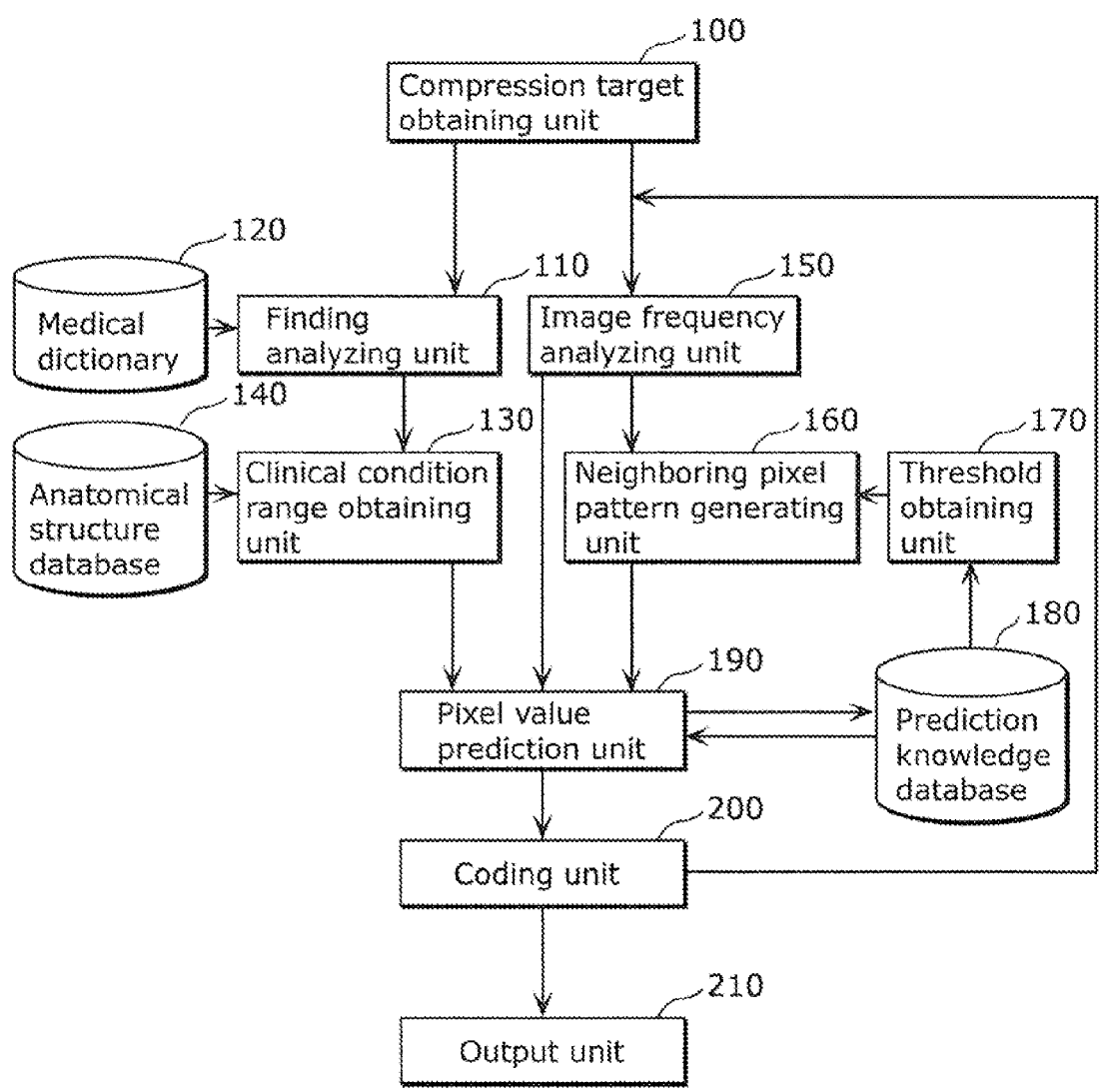
FIG. 1 is a block diagram illustrating a functional configuration of a medical image compression device according to Embodiment 1.

A medical image compression device according to an exemplary embodiment disclosed herein includes: a compression target obtaining unit configured to obtain (i) a target image which is a medical image to be compressed and (ii) diagnostic finding information for the target image; a clinical condition range obtaining unit configured to divide the target image into regions each corresponding to a different one of clinical conditions based on the diagnostic finding information; a pixel value prediction unit configured to, for an arbitrary pixel, refer to a prediction knowledge database in which an appearance distribution of a pixel value of an arbitrary pixel is stored for each of the clinical conditions, and calculate a prediction probability of a pixel value of a prediction target pixel based on the clinical condition of the prediction target pixel and the appearance distribution of the pixel value of the prediction target pixel, the appearance distribution of the pixel value of the arbitrary pixel corresponding to a pixel value included in a predetermined neighboring range; a coding unit configured to code the pixel value of the prediction target pixel based on the prediction probability of the pixel value calculated by the pixel value prediction unit; and an output unit configured to output a code of the prediction target pixel after being coded by the coding unit.

According to this configuration, the medical image compression device divides, by utilizing diagnostic finding information, a target image into regions each of which corresponds to a different one of clinical conditions. In addition, by predicting a pixel value of a prediction target pixel with use of, as knowledge, an appearance distribution of a pixel value which corresponds to (i) the clinical condition obtained from a past case and (ii) a pixel value of a pixel included in a neighboring range, it is possible to predict a pixel value suitable to an image (a medical image, in this case) of a target for compression. For that reason, it is possible to compress a medical image with high compression efficiency and a lossless scheme.

For example, the diagnostic finding information may include at least information related to the clinical condition and a position of the clinical condition, as a result of an examination for diagnosis of the target image by a doctor, the medical image compression device may further include: a finding analyzing unit configured to refer to a medical dictionary in which (i) a clinical condition keyword which is a term indicating a clinical condition and (ii) a position keyword which is a term indicating a position of the clinical condition are held, and extract the clinical condition keyword and the position keyword from the diagnostic finding information obtained by the compression target obtaining unit; an image frequency analyzing unit configured to perform frequency analysis on the target image obtained by the compression target obtaining unit; and a neighboring pixel pattern generating unit configured to generate, in the target image, a neighboring pixel pattern including pixel values of pixels included in a predetermined range which includes neighboring pixels of the prediction target pixel, the target image being the target image on which the frequency analysis has been performed by the image frequency analyzing unit, the clinical condition range obtaining unit may refer to an anatomical structure database in which the position keyword and range information of a clinical condition on a medical image are held in association with each other, and obtain range information of a clinical condition on the target image which is obtained by the compression target obtaining unit, the range information of the clinical condition on the target image corresponding to the position keyword extracted by the finding analyzing unit, the prediction knowledge database may hold a plurality of items of row data including (i) the clinical condition keyword, (ii) the pixel values of pixels included in the predetermined range which includes the neighboring pixels of an arbitrary pixel, and (iii) the appearance distribution of the pixel value of the arbitrary pixel, and the pixel value prediction unit may refer to the prediction knowledge database to obtain the row data including the clinical condition keyword extracted by the finding analyzing unit and the neighboring pixel pattern generated by the neighboring pixel pattern generating unit, and calculate a prediction probability of the pixel value of the prediction target pixel based on the appearance distribution of the pixel value of the arbitrary pixel included in the obtained row data.

According to this configuration, the medical image compression device figures out a clinical condition and information on a range of the clinical condition, by utilizing the diagnostic finding information. In addition, the medical image compression device generates a pattern (neighboring pixel pattern) of pixel values in a neighboring pixel region, which is to be used for predicting a pixel value from an image on which frequency analysis has been performed. Furthermore, by predicting a pixel value of a prediction target pixel with use of, as knowledge, an appearance distribution of an actual pixel value which corresponds to (i) the clinical condition obtained from a past case and (ii) the neighboring pixel pattern, it is possible to predict a pixel value suitable to an image (a medical image, in this case) of a target for compression. For that reason, it is possible to compress a medical image with high compression efficiency and a lossless scheme.

For example, the neighboring pixel pattern generating unit may generate, as the neighboring pixel pattern, a pattern including a pixel value larger than or equal to a threshold, among pixel values of a pixel included in the predetermined range which includes the neighboring pixels of the prediction target pixel, in the target image on which the frequency analysis has been performed by the image frequency analyzing unit.

A pixel having a large pixel value in an image on which frequency analysis has been performed is a pixel having a large amount of information. For that reason, it is possible to generate a neighboring pixel pattern of pixels having a large amount of information. With this, it is possible to predict a pixel value of a prediction target pixel with accuracy.

In addition, the neighboring pixel pattern generating unit may generate, as the neighboring pixel pattern, a pattern which includes a pixel value larger than or equal to the threshold corresponding to the clinical condition keyword extracted by the finding analyzing unit, among the pixel values of the pixels included in the predetermined range which includes the neighboring pixels of the prediction target pixel, in the target image on which the frequency analysis has been performed by the image frequency analyzing unit.

Use of the threshold suitable to the clinical condition as described above makes it possible to generate a neighboring pixel pattern reflecting the complexity or characteristics of texture according to the clinical condition. This allows prediction with higher accuracy, and as a result, it is possible to improve the compression efficiency.

In addition, when the pixel value prediction unit cannot obtain the row data, the neighboring pixel pattern generating unit may further update the threshold to a value larger than a current value, and generate the neighboring pixel pattern using the threshold resulting from the update.

It is possible to generate a neighboring pixel pattern having a range narrower than a current range, by updating a threshold to have a value larger than a current value. For that reason, in the case of a neighboring pixel pattern having a broad range, even when a corresponding frequency distribution is not present in the prediction knowledge database, the possibility that the corresponding frequency distribution can be obtained increases by re-setting the neighboring pixel pattern to be narrow.

In addition, when the pixel value prediction unit cannot obtain the row data even when the threshold resulting from the update is used, the pixel value prediction unit may further refer to the prediction knowledge database to obtain row data including (i) a clinical condition keyword different from the clinical condition keyword extracted by the finding analyzing unit and (ii) the neighboring pixel pattern generated by the neighboring pixel pattern generating unit, and calculate a prediction probability of the pixel value of the prediction target pixel, based on the appearance distribution of the pixel value of the arbitrary pixel included in the obtained row data.

According to this configuration, even when an appearance distribution is not present in the prediction knowledge database even after changing the neighboring pixel pattern, it is possible to predict a pixel value using the appearance distribution created for a different clinical condition.

In addition, when the number of appearance of the pixel value of the arbitrary pixel is 0, the pixel value prediction unit may calculate a predetermined value larger than 0 as the prediction probability of the pixel value of the prediction target pixel.

According to this configuration, it is possible to perform coding even when a coding method with which a pixel value having a prediction probability of 0 cannot be coded is employed.

In addition, the pixel value prediction unit may dynamically change the predetermined value larger than 0, according to a sporadic rate of the arbitrary pixel having a pixel value with a number of appearance of 0 in a latest process which is performed for a predetermined number of times.

A prediction knowledge database creation device according to another aspect of the present disclosure is a prediction knowledge database creation device which creates a prediction knowledge database for use in the medical image compression device described above, the prediction knowledge database creation device including: a case selecting unit configured to select a nonselected case from a case database as a result of an examination for diagnosis of the medical image by a doctor, the case database holding a plurality of cases each including a medical image and diagnostic finding information which includes at least a clinical condition and information related to a position of the clinical condition; a finding analyzing unit configured to refer to a medical dictionary in which (i) a clinical condition keyword which is a term indicating a clinical condition and (ii) a position keyword which is a term indicating a position of the clinical condition are held, and extract the clinical condition keyword and the position keyword from the diagnostic finding information included in the case selected by the case selecting unit; the clinical condition range obtaining unit configured to refer to an anatomical structure database in which the position keyword and range information of a clinical condition on a medical image are held in association with each other, and obtain range information of a clinical condition on the medical image, which corresponds to the position keyword extracted by the finding analyzing unit and included in the case selected by the case selecting unit; an image frequency analyzing unit configured to perform frequency analysis on the medical image included in the case selected by the case selecting unit; a neighboring pixel pattern generating unit configured to generate a neighboring pixel pattern including pixel values of pixels included in a predetermined range which includes neighboring pixels of a target pixel, in the medical image on which the frequency analysis has been performed by the image frequency analyzing unit, and a pixel value frequency distribution updating unit configured to obtain, from the prediction knowledge database, row data corresponding to the clinical condition keyword extracted by the finding analyzing unit and the neighboring pixel pattern generated by the neighboring pixel pattern generating unit, and update, using the pixel value of the target pixel, an appearance distribution of a pixel value of an arbitrary pixel included in the obtained row data.

According to this configuration, the prediction knowledge database creation device obtains, with use of the diagnostic finding information, a clinical condition and information on a range of the clinical condition. In addition, the prediction knowledge database creation device generates a pattern (neighboring pixel pattern) of pixel values in a neighboring pixel region, which is to be used for predicting a pixel value from an image on which frequency analysis has been performed. In addition, it is possible to construct a prediction knowledge database with use of, as knowledge, an appearance distribution of an actual pixel value, which corresponds to the clinical condition obtained from a past case and a neighboring pixel pattern. By predicting a pixel value of a prediction target pixel with use of such a prediction knowledge database, it is possible to predict a pixel value suitable to an image (a medical image, in this case) of a target for compression. For that reason, it is possible to compress a medical image with high compression efficiency and a lossless scheme.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Embodiment 1

FIG. 1 is a block diagram illustrating a functional configuration of a medical image compression device according to Embodiment 1.

The medical image compression device includes: a compression target obtaining unit 100; a finding analyzing unit 110; a medical dictionary 120; a clinical condition range obtaining unit 130; an anatomical structure database 140; an image frequency analyzing unit 150; a neighboring pixel pattern generating unit 160; a threshold obtaining unit 170; a prediction knowledge database 180; a pixel value prediction unit 190; a coding unit 200; and an output unit 210.

The compression target obtaining unit 100 obtains a medical image of a compression target and diagnostic finding information entered when the medical image is examined for diagnosis by a doctor. The compression target obtaining unit 100, for example, may obtain the medical image and the diagnostic finding information by user's input, or may obtain the medical image and the finding information from a predetermined case database. The medical image of the compression target obtained by the compression target obtaining unit 100 is hereinafter also referred to as a target image.

The finding analyzing unit 110 (i) refers to the medical dictionary 120 in which a term indicating a clinical condition and a term indicating a position of the clinical condition, that is, a position at which the clinical condition is developed (for example, a term indicating an anatomical structure) are stored, (ii) analyzes the diagnostic finding information obtained by the compression target obtaining unit 100, and (iii) extracts a keyword in the format which includes the term indicating the clinical condition and the term indicating the position of the clinical condition as a set. Hereafter, the term indicating a clinical condition is referred to as a clinical condition keyword, and the term indicating a position of the clinical condition is referred to as a position keyword.

The clinical condition range obtaining unit 130 (i) refers to the anatomical structure database 140 in which the position keyword and range information (a coordinate at which the clinical condition is present) of a clinical condition on a medical image are stored in association with each other, and (ii) obtains the range information of the clinical condition which is on the target image obtained by the compression target obtaining unit 100 and corresponds to the position keyword extracted by the finding analyzing unit 110. With this, the clinical condition range obtaining unit 130 replaces the position keyword with the coordinate in the target image.

The image frequency analyzing unit 150 performs frequency analysis on the target image obtained by the compression target obtaining unit 100.

The neighboring pixel pattern generating unit 160 generates a pattern of pixel values of neighboring pixels (hereinafter referred to as a neighboring pixel pattern) for use in predicting a pixel value of a prediction target pixel included in the target image, based on (i) the image on which frequency analysis has been performed by the image frequency analyzing unit 150 and (ii) the threshold obtained by the threshold obtaining unit 170 that will be described later. It is to be noted that, in the description below, an arrangement pattern of the neighboring pixels is also referred to as a neighbor pattern in some cases. Specifically, the neighboring pixel pattern generating unit 160 generates, in the image on which frequency analysis has been performed, a neighboring pixel pattern including pixel values of pixels included in a predetermined range which includes the neighboring pixels of the prediction target pixel. More specifically, the neighboring pixel pattern generating unit 160 generates, as a neighboring pixel pattern, a pattern including pixel values which are greater than or equal to a threshold among the pixel values of the pixels included in the above-described predetermined range, in the image on which frequency analysis has been performed.

The prediction knowledge database 180 holds a plurality of items of row data which includes (i) a clinical condition keyword, (ii) pixel values of pixels included in the predetermined range which includes the neighboring pixels of an arbitrary pixel in the medical image, and (iii) an appearance distribution of the pixel value of the arbitrary pixel. A specific example of the prediction knowledge database 180 will be described later. Other than that, the prediction knowledge database 180 stores a threshold necessary for generating a neighboring pixel pattern.

The threshold obtaining unit 170 obtains, from the prediction knowledge database 180, a threshold which will be necessary when generating a neighboring pixel pattern.

The pixel value prediction unit 190 (i) refers to the prediction knowledge database 180, (ii) obtains the clinical condition keyword extracted by the finding analyzing unit 110 and the row data including the neighboring pixel pattern generated by the neighboring pixel pattern generating unit 160, and (iii) calculates a prediction probability of a pixel value of the prediction target pixel, based on the appearance distribution of the pixel value of the arbitrary pixel included in the obtained row data.

The coding unit 200 codes the pixel value of the prediction target pixel, based on the prediction probability of the pixel value calculated by the pixel value prediction unit 190.

The output unit 210, when all of the pixels in the target image are coded by the coding unit 200, outputs, as compressed data, the code of the prediction target pixel which has been coded by the coding unit 200.

Figure 2:
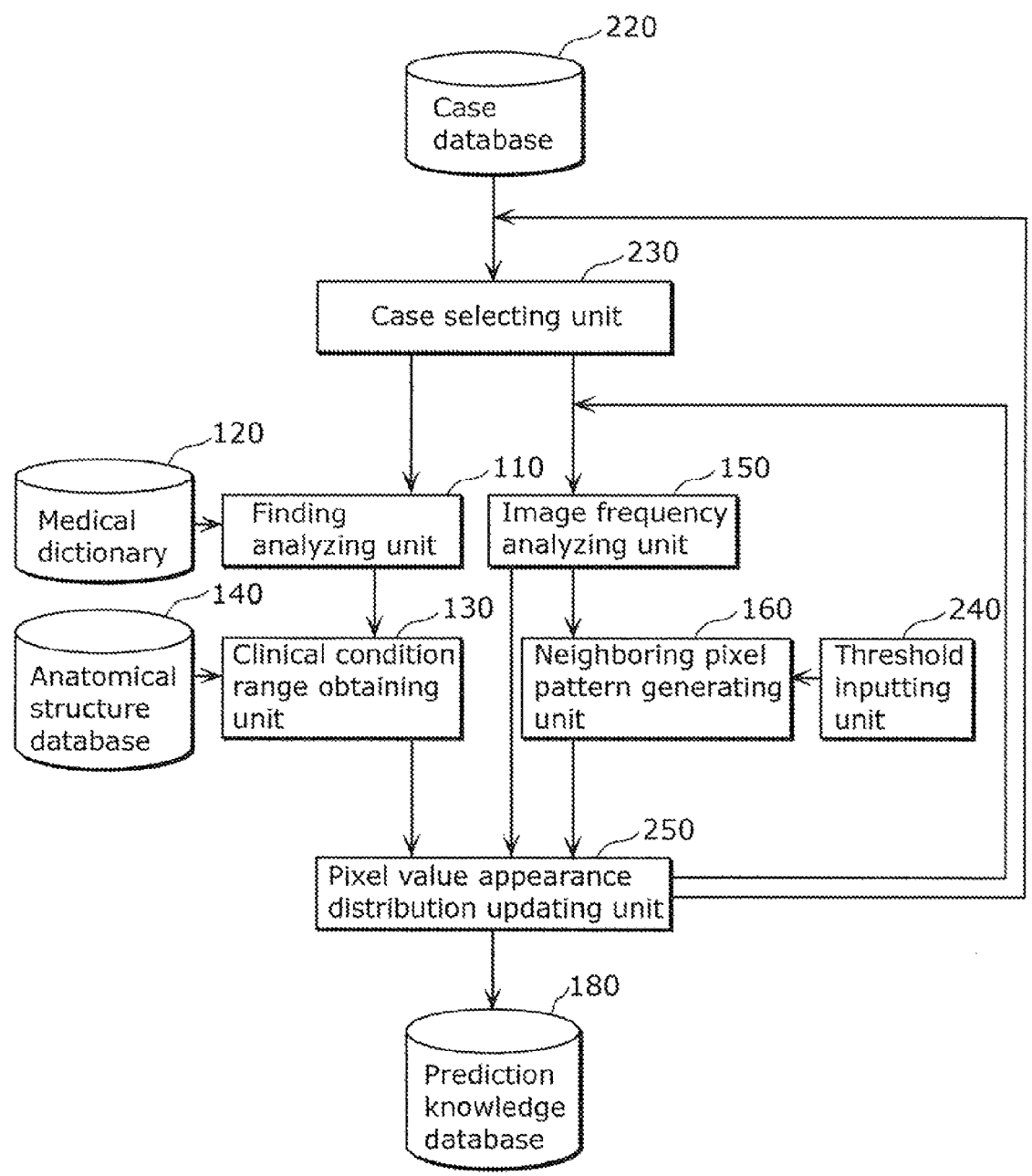
FIG. 2 is a block diagram illustrating a functional configuration of a prediction knowledge database creation device according to Embodiment 1.

FIG. 2 is a block diagram illustrating a functional configuration of the prediction knowledge database creation device which creates the prediction knowledge database 180 which is used at the time of compressing a medical image.

The prediction knowledge database creation device includes: a case database 220; a case selecting unit 230; the finding analyzing unit 110; the medical dictionary 120; the clinical condition range obtaining unit 130; the anatomical structure database 140; the image frequency analyzing unit 150; the neighboring pixel pattern generating unit 160; a threshold inputting unit 240; a pixel value frequency distribution updating unit 250; and the prediction knowledge database 180.

The case database 220 stores a plurality of "cases" each including a pair of (i) a medical image such as computed tomography (CT) and magnetic resonance imaging (MRI) and (ii) diagnostic finding information (report) as a result of an examination for diagnosis of the medical image by a doctor, which contains at least a clinical condition and information related to the position of the clinical condition.

The case selecting unit 230 selects one nonselected case from the case database 220.

The finding analyzing unit 110 refers to the medical dictionary 120 in which the clinical condition keywords and the position keywords (terms indicating the anatomical structures) are stored, and extracts a keyword in the format which includes the clinical condition keyword and the position keyword as a set, from the diagnostic finding information items included in the case selected by the case selecting unit 230.

The clinical condition range obtaining unit 130 refers to the anatomical structure database 140 in which the position keyword and the range information (a coordinate at which the clinical condition is present) of a clinical condition on a medical image are stored in association with each other, and obtains the range information of the clinical condition on the medical image included in the case selected by the case selecting unit 230, which corresponds to the position keyword extracted by the finding analyzing unit 110. With this, the clinical condition range obtaining unit 130 replaces the position keyword with the coordinate in the medical image.

The image frequency analyzing unit 150 performs frequency analysis on the medical image included in the case selected by the case selecting unit 230.

The neighboring pixel pattern generating unit 160 generates the pattern of pixel values of neighboring pixels (neighboring pixel pattern) for use in predicting a pixel value of a target pixel in the image on which frequency analysis has been performed, based on: the image on which frequency analysis has been performed by the image frequency analyzing unit 150; and the threshold obtained by the threshold obtaining unit 240. More specifically, the neighboring pixel pattern generating unit 160 generates, in the image on which frequency analysis has been performed, a neighboring pixel pattern including pixel values of pixels included in a predetermined range which includes the neighboring pixels of the target pixel.

The threshold inputting unit 240 obtains a threshold to be used in a process performed by the neighboring pixel pattern generating unit 160. The way of obtaining the threshold is not limited, and the threshold inputting unit 240 may obtain the threshold by user's input, or may obtain the threshold from a storage device in which the threshold is stored in advance.

The pixel value frequency distribution updating unit 250 updates and stores, into the prediction knowledge database 180, the appearance distribution of the pixel value with use of, as the keys, the clinical condition keyword extracted by the finding analyzing unit 110, the image after frequency analysis generated by the image frequency analyzing unit 150, and the neighboring pixel pattern generated by the neighboring pixel pattern generating unit 160. More specifically, the pixel value frequency distribution updating unit 250 (i) obtains, from the prediction knowledge database 180, the row data corresponding to the clinical condition keyword and the neighboring pixel pattern, and (ii) updates, with use of the pixel value of the target pixel, the appearance distribution of the pixel value of an arbitrary pixel included in the obtained row data. It is to be noted that, when the corresponding row data is not included in the prediction knowledge database 180, the pixel value frequency distribution updating unit 250 newly creates row data.

The following describes the operations performed by the respective elements according to one or more exemplary embodiments describes in detail.

[Preparation of Prediction Knowledge Database]

Figure 3:
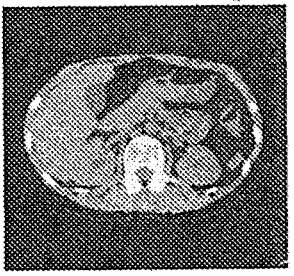
FIG. 3 is a diagram illustrating an example of a case database.

Prior to compressing a medical image, the prediction knowledge database creation device obtains, in advance, the knowledge to be used for predicting a pixel value, and stores the knowledge into the prediction knowledge database 180. The prediction knowledge database 180 can be obtained from a plurality of accumulated "cases" each including a pair of a medical image and diagnostic finding information entered when the medical image is examined for diagnosis by a doctor. The cases stored in the case database 220 are used. FIG. 3 illustrates an example of the case database. The case database 220 is a database which includes a large number of cases each of which includes the medical image and the diagnostic finding information as a set.

In this exemplary embodiment, the clinical condition of an arbitrary pixel portion and the appearance distribution of the pixel value of the arbitrary pixel according to a pattern (neighboring pixel pattern) of the pixel values of the neighboring pixels used for prediction are employed as the prediction knowledge of the pixel value. In performing the prediction, the clinical condition and the appearance distribution of the pixel value corresponding to the neighboring pixel pattern are referred to, and the prediction probability of each of the pixel values is calculated.

Figure 4:
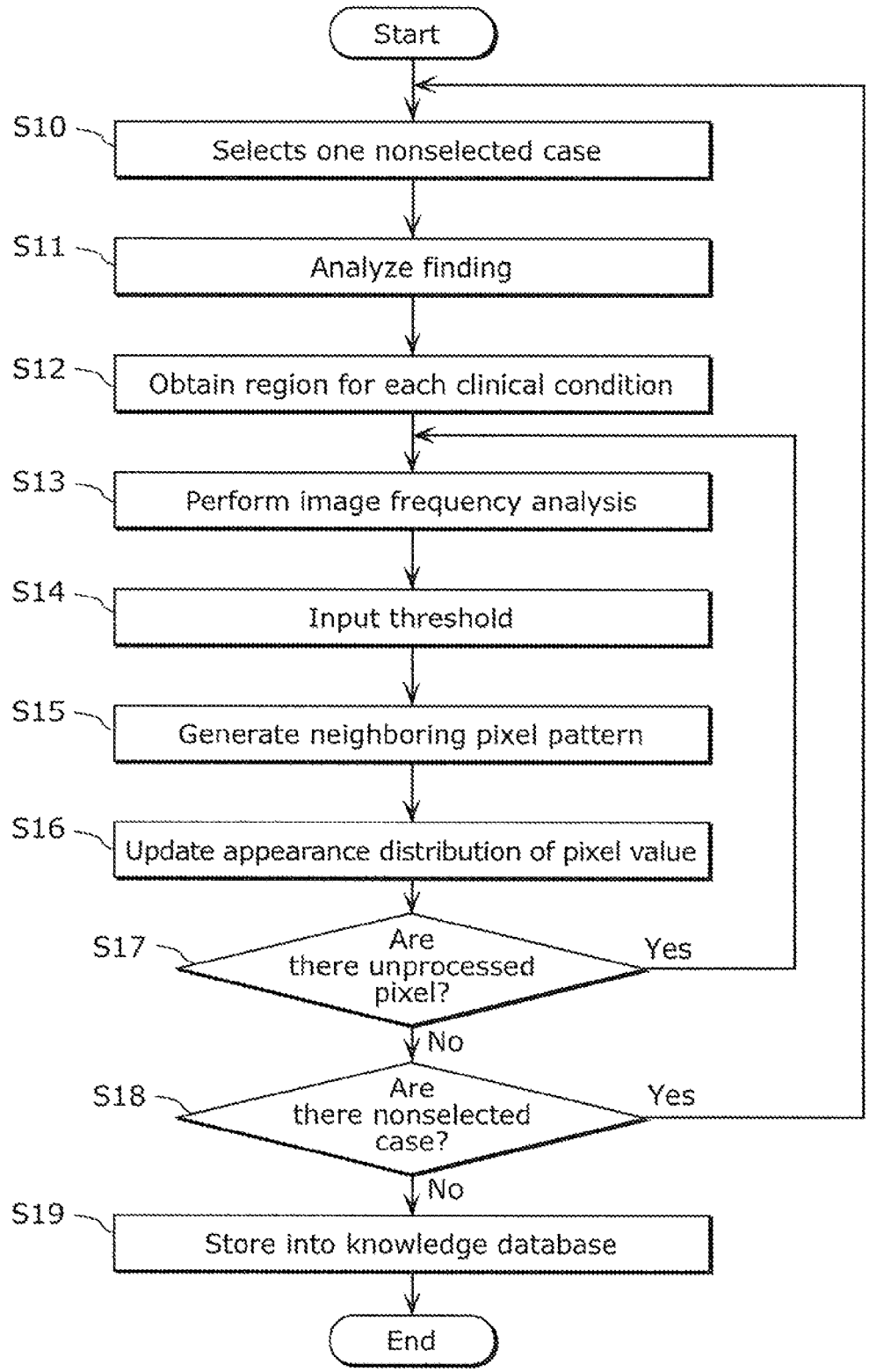
FIG. 4 is a flowchart illustrating a procedure of prediction knowledge creation according to Embodiment 1.

The following describes the procedure for the prediction knowledge creation, with use of the flowchart illustrated in FIG. 4. The medical image which is a target in this exemplary embodiment is assumed to be an abdominal CT image.

In Step S10, the case selecting unit 230 selects one nonselected case from the case database 220 in which cases for obtaining prediction knowledge are stored. Each case includes a set of a medical image and diagnostic finding information entered when a doctor examines the medical image for diagnosis. It is to be noted that, when the medical image is obtained by a multi-detector computed tomography, a single case includes a large number of slice images. In an examination in which a contrast medium is employed, image capturing is carried out several times, with time intervals, in one examination. In this case, a set of a large number of slice images is obtained for each image capturing, and these images are included in a single case.

In Step S11, the finding analyzing unit 110 analyzes the diagnostic finding information of the obtained case. To be more specific, the finding analyzing unit 110 (i) refers to the medical dictionary 120, (ii) extracts the clinical condition keyword and the position keyword from the diagnostic finding information, and (iii) outputs the clinical condition keyword and the position keyword in the set format such as (the position keyword, the clinical condition keyword). The clinical condition keyword, which includes a disease name such as "hepatocyte cancer", "angioma", and "cyst", also includes a term other than the disease name, such as a "normal portion". Furthermore, the clinical condition keyword may include, in addition to the disease name, a keyword describing how a clinical condition looks on an image, such as "early stain", "LDA", and "ring-shaped stain". The position keyword includes, in addition to the organ names such as "lung", "liver", and "pancreas", terms such as "right lung", "left lung", "(liver) right lobe", and "(liver) left lobe" each of which describes a general position of the organ, and terms such as "S1", "S2", and "S3" each of which indicates an anatomical region of the organ. In this exemplary embodiment, a morpheme analysis and a syntax analysis are made using the medical dictionary 120 in which terms (position keywords) indicating the clinical condition keywords and the anatomical structures are stored, thereby extracting the clinical condition keyword and the position keyword. Examples of morpheme analysis techniques include Non-patent Literature: MeCab (http://mecab.sourceforge.net), Non-patent Literature: ChaSen (http://chasen-legacy.sourceforge.jp), and so on, and examples of syntax analysis techniques include Non-patent Literature: KNP (http://nlp.Kuee.kyoto-u.ac.jp/nl-resource/knp.html), Non-patent Literature: CaboCha (http://chasen.org/~taku/software/cabocha/), and so on.

The diagnostic finding information is often described using unique expressions by a doctor, and thus it is desirable to develop morpheme analysis techniques, syntax analysis techniques, and various word dictionaries which are exclusive for the diagnostic finding information. The simplest method of associating a clinical condition and a position is to associate the clinical condition and the position which has appeared immediately before the clinical condition in the text of the diagnostic finding information. In the case of the diagnostic finding information analysis, association can be done in many cases even with such a simple method, however, association can also be done with higher accuracy using a result of the syntax analysis described above.

FIG. 5 is an example of the diagnostic finding information obtained by the abdominal CT scan and FIG. 6 is an exampled of extracting the clinical condition keyword and the position keyword in a set from the diagnostic finding information. In the case of FIG. 6, only the disease name is extracted as the clinical condition keyword. However, as in FIG. 7, a term (image diagnostic finding information) describing how a clinical condition looks on an image may be extracted and used as the clinical condition keyword. In addition, FIG. 8 illustrates an example of also extracting information on a time phase concurrently with the clinical condition keyword and the position keyword. As described above, when the contrast medium examination is performed using the multi-detector computed tomography or the like, sets of a plurality of images are combined together in some cases. In such a case, further detailed association, indicating which keyword indicates which image, for example, is made possible by obtaining the information on a time phase.

In Step S12, the clinical condition range obtaining unit 130 transforms the position keyword obtained in Step S11 into a coordinate on the image. In this exemplary embodiment, the anatomical structure database 140 which holds the correspondence relationship between the position keyword and the coordinate on the image is employed.

Figures 9, 10:
FIG. 9 is a diagram illustrating the case where a correspondence between the position keyword (Liver S6) and a range on an image is represented by a rectangle region, according to Embodiment 1.
FIG. 10 is a diagram illustrating an example of an anatomical structure database (the case where a range is held as a rectangle region), according to Embodiment 1.
Figures 11, 12, 13:
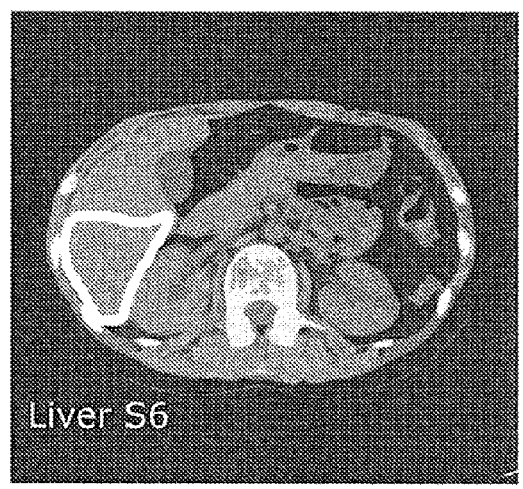
FIG. 11 is a diagram illustrating the case where a correspondence between the position keyword (Liver S6) and a range on an image is represented by a complicated region, according to Embodiment 1.
FIG. 12 is a diagram illustrating the structure of the anatomical structure database (the case where a range is held as a complicated region), according to Embodiment 1.
FIG. 13 is a diagram illustrating the case where the position keyword is transformed into a coordinate on the image, according to Embodiment 1.

To put it simply, the anatomical structure database 140 holds the correspondence relationship between the position keyword and the coordinate indicating a rectangle region on the image as illustrated in FIG. 9. Accordingly, the anatomical structure database 140 has a structure as shown in FIG. 10. In the range (X1, Y1)-(X2, Y2) shown in the table, (X1, Y1) indicates an upper left coordinate of the rectangle region, and (X2, Y2) indicates a lower right coordinate of the rectangle region. Since the anatomical structure database 140 is created in such a format, the size of the anatomical structure database 140 can advantageously be compact. In addition, other formats of the anatomical structure database 140 include a format in which a position keyword and a complicated region on the coordinate are associated with each other, as in FIG. 11. In sum, the anatomical structure database 140 has the structure as shown in FIG. 12. In this format, all the coordinates on an image which corresponds to a position keyword are stored in the anatomical structure database 140. This format has an advantageous effect that it is possible to obtain a detailed and accurate clinical condition range, compared to the case where the clinical condition range is represented by a rectangle region as in FIG. 10.

It is to be noted that, although the clinical condition range is represented by a two-dimensional coordinate represented by (X, Y) in this exemplary embodiment, when a target medical image is an image having a three-dimensional structure, such as CT or MR, it is desirable that the clinical condition range is represented by a three-dimensional coordinate including a Z axis direction, to construct the anatomical structure database 140. In addition, although the correspondence relationship between the position keyword and the clinical condition range for only the liver portion is described in the examples of the anatomical structure database 140 illustrated in FIG. 10 and FIG. 12, the anatomical structure database 140 holds similar correspondence relationship for all the organs such as the lung, the pancreas, the kidney, and so on.

FIG. 13 illustrates an example of a result of transforming, by the clinical condition range obtaining unit 130, a position keyword into a range (coordinate on the image). In this example, the result of the case where the simple anatomical structure database 140 which represents the clinical condition range by a rectangle region is indicated.

When the clinical condition range is obtained according to the processes as described above, a problem may arise that a plurality of clinical conditions are overlapped. For example, when (Liver, LC pattern) and (Liver S3, Hepatocyte cancer) are extracted as the keywords of the combination of (position keyword, clinical condition keyword), the "Liver S3" is included in the "Liver". For that reason, the clinical conditions are overlapped. In a portion where a plurality of clinical conditions are overlapped as described above, a clinical condition of the position keyword representing the more detailed region (here, "Liver S3") is employed. To be more specific, in the portion where clinical conditions are overlapped, a clinical condition range having the smallest area when the position keyword is transformed into a range is employed as the clinical condition range.

It is to be noted that a region having no particular description about a clinical condition is assumed to be a normal portion. This is because a doctor does not particularly give a description on the diagnostic finding information for the portion with no lesions. Through the processes described above, it is possible to obtain a correspondence relationship which represents to which clinical condition an arbitrary coordinate belongs on an image.

In Step S13, the image frequency analyzing unit 150 performs frequency analysis on an input medical image (target image). The purpose of the image frequency analysis in this step is to determine which pattern (neighboring pixel pattern) of pixel values of neighboring pixels are to be used for predicting a pixel value of a pixel. In this exemplary embodiment, wavelet transformation is employed as a method of performing frequency analysis on an image. When the frequency analysis (wavelet transformation) is performed, there is a feature that a value becomes great in a region having a large amount of information. In other words, by performing the frequency analysis and determining, as a neighboring pixel pattern, only the pixel values of a portion with a value greater than or equal to a predetermined value, it is possible to predict a pixel value using a neighboring pixel region having a large amount of information. With the wavelet transformation, a process of taking difference from an adjacent pixel is repeatedly performed. At this time, although the process is performed per pixel in the first step, the process is performed per $n^2 \times n^2$ region in the nth step of the wavelet transformation. At this time, the value of the $n^2 \times n^2$ region is an average value of all of the pixels included in the region. In this step, the frequency analysis (wavelet transformation) is performed on the upper left region of the prediction target pixel. This is because, in this exemplary embodiment, it is assumed that compression is performed on one pixel at a time sequentially from the upper left pixel. Since only the pixels which have already been compressed can be used for the prediction (because using a pixel other than compressed ones disables decompression), the pixel value of a target pixel is predicted starting from the upper left region pixel in this case. For that reason, although the frequency analysis is performed on the upper left region in this exemplary embodiment, the region on which the frequency analysis is performed changes according to the order of the pixel to be compressed, and it is not necessarily limited to the upper left region.

The pixel value of the prediction target pixel is not obtained at the time of decoding, and thus analysis is carried out from the second step of the wavelet transformation using an average of adjacent three pixels (upper, upper left, left) as an average value of 2×2 region. FIG. 14 is a diagram illustrating an example of a prediction target pixel. A pixel X located at the lower right in FIG. 14 represents a pixel to be coded. FIG. 15 is a diagram illustrating an example of the case where the wavelet transformation is performed on the image illustrated in FIG. 14 according to the method of this step. As described above, the value of X is unknown at the time of decoding, and thus transformation is performed by regarding the average value of the pixel values 64, 61, and 58 of the neighboring pixels as the average values of 2×2 region. It is to be noted that, as to the handling of the value of X, a prediction value may be determined by pixel value prediction algorithm used conventionally, such as Low Complexity Lossless Compression for Images (LOCO-I), other than the average value of neighboring three pixels, and this exemplary embodiment does not put a limit on the handling of X.

In Step S14, the threshold inputting unit 240 obtains a threshold for generating a neighboring pixel pattern. In this exemplary embodiment, only a predetermined value is read. However, it is also possible to adjust an appropriate value in advance, or prepare a plurality of thresholds for each clinical condition. The details will be described in Embodiment 2.

Figure 16:
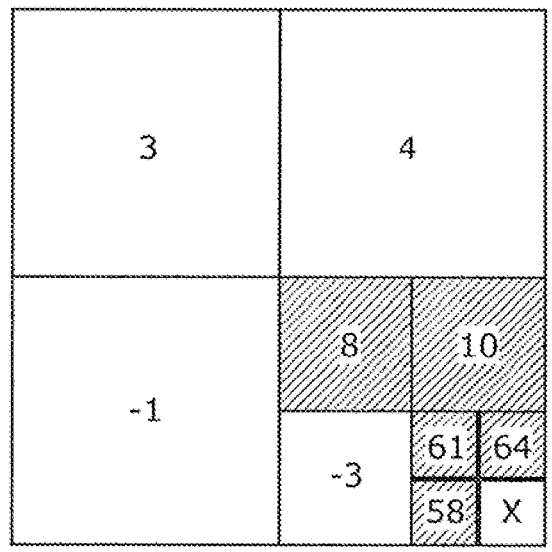
FIG. 16 is a diagram illustrating an example of neighboring pixel pattern generated when the threshold is set to five, according to Embodiment 1.

In Step S15, the neighboring pixel pattern generating unit 160 generates a pattern (neighboring pixel pattern) of the pixel value of the region to be used in predicting a pixel value. To be more specific, in the frequency-analyzed image generated in Step S13, only a region in which change of the pixel value (the absolute value of the difference between the pixel values, the absolute value of the wavelet coefficient) is greater than or equal to the threshold is extracted, and the pattern of the pixel values included in the region is determined as the neighboring pixel pattern. With the step as described above, it is possible to use, for prediction of a pixel value, only the portion having a large amount of information among the neighboring pixels of the prediction target pixel. The value obtained in Step S14 is used as the threshold, FIG. 16 illustrates an example of generating a neighboring pixel pattern from the neighboring pixels after the frequency analysis shown in FIG. 15. In this example, the pixels included in the neighboring pixel pattern when the threshold is set to five are illustrated by hatching. At the time of compression, the pixel value of the pixel X is predicted using the pixels in the cells to which hatching is applied in FIG. 16.

Figure 17:
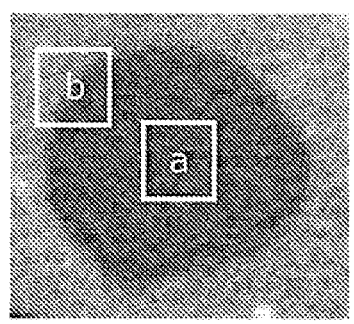
FIG. 17 is a diagram illustrating an example of the difference between the neighboring pixel patterns generated according to the texture of a region, according to Embodiment 1.

FIG. 17 is a diagram illustrating the case where a neighboring pixel pattern is generated for a CT image of a liver tumor. When a neighboring pixel pattern is generated in the region a near the center of the tumor, a small neighboring pixel pattern is generated. This is because, since a luminance change is small in the tumor in the case of this tumor (cyst), the pixel value exceeds a threshold in an early phase when threshold processing is performed after the wavelet transformation, however, the luminance change between pixels decreases as passing thorough the phases due to the effect of smoothing, and the change does not exceed the threshold. In the case of such a portion as the region a, it is obvious that there is not a significant difference in information to be obtained broadly from neighboring pixels, and thus it can be said that an appropriate neighboring pixel pattern is generated.

In addition, when the neighboring pixel pattern is generated in a portion including texture and an edge portion as in the region b, it can be seen that a large neighboring pixel pattern is generated. In a portion having a complicated texture or an edge portion, it is difficult to perform prediction of a pixel value with a high accuracy using only the adjacent pixels, and thus the large neighboring pixel pattern such as the one generated is more suitable to be used for prediction.

In Step S16, the pixel value frequency distribution updating unit 250 updates an appearance distribution of an actual pixel value which corresponds to the clinical condition obtained in Step S12 and the neighboring pixel pattern generated in Step S15. The following describes the details of a configuration of the prediction knowledge database 180 and the update processing thereof.

[Configuration of Prediction Knowledge Database 180]

Figure 19:
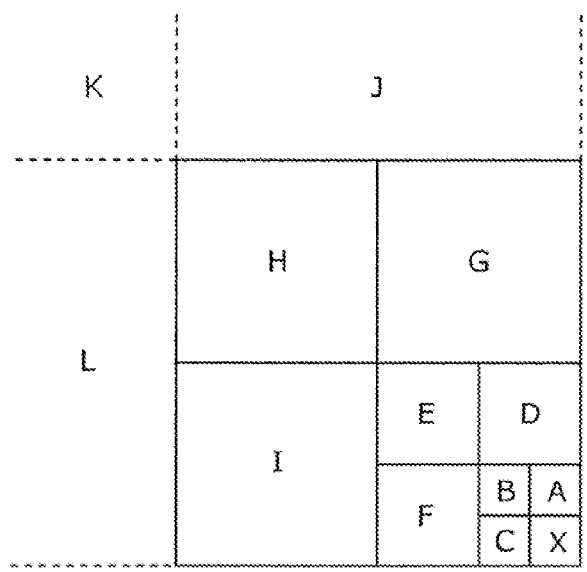
FIG. 19 is a diagram illustrating a depiction of a neighboring pixel pattern in the prediction knowledge database in FIG. 18 according to Embodiment 1.
Figure 20:
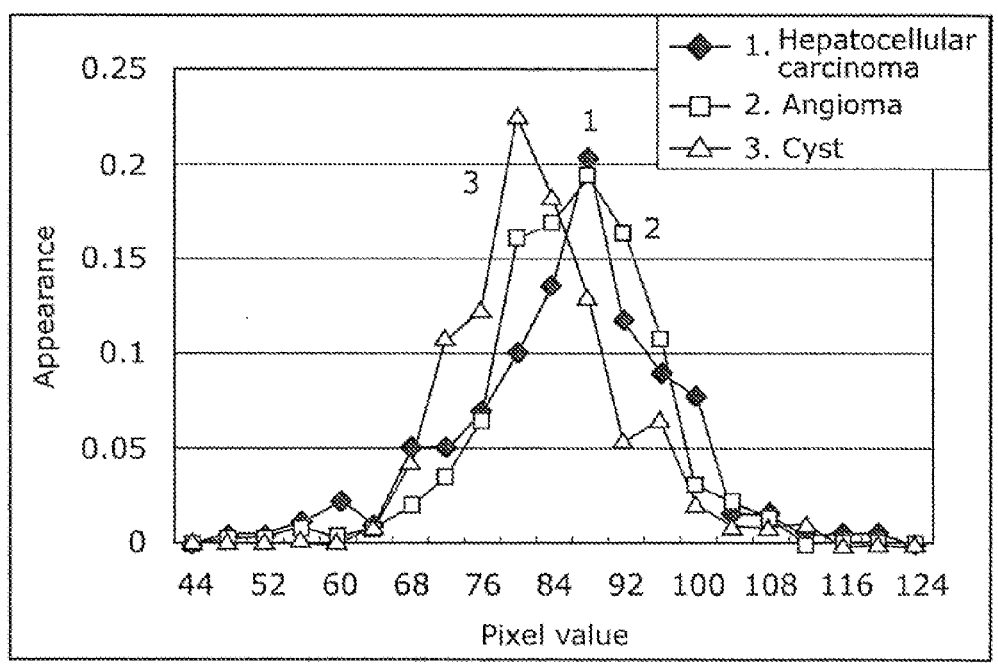
FIG. 20 is a diagram illustrating an example of the difference between pixel value distributions according to clinical conditions when the neighboring pixels are the same (the case of 520 liver tumor CT images), according to Embodiment 1.

FIG. 18 illustrates a configuration of the prediction knowledge database 180 according to this exemplary embodiment. In the prediction knowledge database 180, the appearance distribution of a pixel value is recorded so as to indicate what pixel has actually appeared when a certain clinical condition and a certain neighboring pixel pattern appeared. The denotations A, B, C, D, E, F G, H, . . . of the neighboring pixels correspond to the positions of the neighboring pixel pattern illustrated in FIG. 19. In FIG. 18, the portions having diagonal lines each represents a portion which is cut off by the threshold and is not included as a neighboring pixel pattern. Since both of the clinical condition and the neighboring pixel pattern are taken into consideration in this prediction knowledge database 180, it is possible to make a prediction according to the respective clinical conditions even when the neighboring pixel pattern is identical as in the case of the second row and the 101th row. The reason for sectioning the rows of the prediction knowledge database 180 by the clinical condition as described above is that distribution of the pixel values of a prediction target pixel differs according to the clinical conditions even when the neighboring pixel pattern is completely identical. FIG. 20 illustrates an appearance distribution of pixel values of an actual pixel X when the same neighboring pixels (the pixel value A located above the target pixel=80, the pixel value C located to the left of the target pixel=88) are included in 520 CT images of a liver tumor.

FIG. 20 illustrates the appearance distributions of three clinical conditions (hepatocyte cancer, angioma, and cyst) illustrated in FIG. 21. As shown by FIG. 20, there is a difference in the distributions of the pixel values between the clinical conditions even when the neighboring pixels are completely identical. For example, the cyst has relatively low pixel values, and the angioma which indicates a complicated texture has a slightly broader distribution compared to the hepatocyte cancer or the like. Such prediction cannot be implemented with the conventional prediction coding, and this is an advantageous point of the present disclosure.

It is to be noted that, the range of a pixel value is assumed to be no less than 0 and no more than 255 according to this exemplary embodiment. However, in the case of a medical image (a variety of radiological images and pathological images), the number of colors such as 10 bit and 12 bit is used in many cases, and an appearance distribution of a color number suitable to the characteristic of a medial image to be compressed is used as necessary.

When the prediction knowledge database 180 is used in prediction, the appearance distribution of actual pixel is referred to using the clinical condition and the neighboring pixel pattern as the keys. The pixel value having a large number of appearances in the appearance distribution can be highly likely to be a pixel value of the prediction target pixel.

[Update of the Appearance Distribution of the Prediction Target Pixel]

The following describes a specific procedure for updating the appearance distribution of the prediction target pixel. In the updating processing (Step S16), the pixel value frequency distribution updating unit 250 updates an appearance distribution corresponding to the clinical condition obtained in Step S12 and the neighboring pixel pattern generated in Step S15. In the case where the clinical condition is hepatocyte cancer and the neighboring pixel pattern is (A, B, C, D, E, F, G, H)=(64, 61, 58, 10, 8, −5, 5, 5), for example, the appearance distribution of the pixel values in the first row of FIG. 18 is updated. It is to be noted that A, B, and C are the pixel values as they are, and other D, E, F, G, and H are values of change of the pixel values. For that reason, the pixels of A, B, and C are used always as the neighboring pixels irrespective of their values.

Here, when the pixel value of the prediction target pixel X is 60, for example, the updated knowledge database is as shown in FIG. 22. In other words, the frequency of the pixel value 60 is updated from 58 to 59.

In addition, as another example, in the case where the clinical condition is cyst, the neighboring pixel pattern is (A, B, C, D)=(60, 61, 60, 5), and the pixel value of the prediction target pixel X is 59, the row corresponding to the clinical condition and the neighboring pixels are not present in FIG. 18. In such a case, a new row is added as in the 104th row in FIG. 23. Use of an appearance distribution created with a sufficient number of cases makes it possible to predict, with high accuracy, a pixel value of the prediction target pixel when a certain clinical condition and a neighboring pixel pattern are provided.

Above-described Steps S13, S14, S15, and S16 are repeatedly performed on all the pixels (Step S17). When all of the pixels are processed, the procedure goes back to Step S10 to select a new case, and the processes of Steps S11, S12, S13, S14, S15, and S16 are performed in the same manner (Step S18). When the processes are performed for all of the cases stored in the case database 220, the procedure goes to Step S19, in which the pixel value frequency distribution updating unit 250 stores, as prediction knowledge, the generated frequency distribution of the pixel value and the threshold used in generating the neighboring pixel pattern, into the prediction knowledge database 180.

[Compression of Medical Image]

Figure 24:
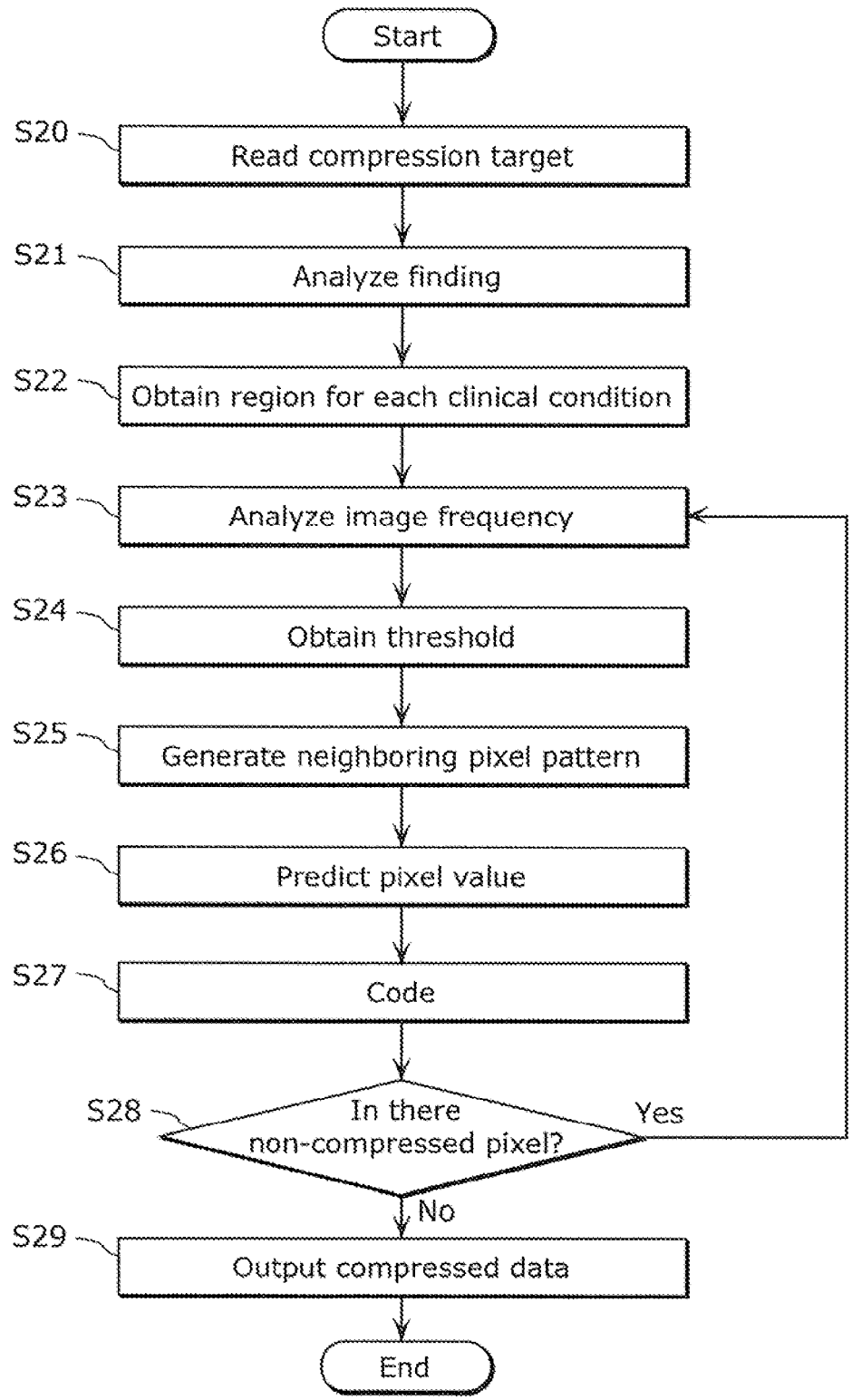
FIG. 24 is a flowchart illustrating a procedure of medical image compression according to Embodiment 1.

The following describes the procedure of medical image compression performed by the medical image compression device illustrated in FIG. 1, with use of the flowchart illustrated in FIG. 24.

In Step S20, the compression target obtaining unit 100 reads a compression target. To be more specific, the compression target obtaining unit 100 reads a set of a medical image (target image) and diagnostic finding information entered when the medical image is examined for diagnosis by a doctor.

In Step S21, the finding analyzing unit 110 extracts a clinical condition keyword and a position keyword as a set, from the entered diagnostic finding information of the compression target. Step S21 can be implemented by performing a similar process to Step S11.

In Step S22, the clinical condition range obtaining unit 130 transforms the position keyword obtained in Step S11 into a coordinate on the image. Step S22 can be implemented by performing a similar process to Step S12.

In Step S23, the image frequency analyzing unit 150 performs frequency analysis on the provided medical image. Step S23 can be implemented by performing a similar process to Step S13.

In Step S24, the threshold obtaining unit 170 obtains, from the prediction knowledge database 180, a threshold necessary for generating a neighboring pixel neighboring pixel pattern. The threshold to be obtained here needs to be the same threshold as the threshold used in creating the prediction knowledge database 180. The threshold may be common among all the clinical conditions or may be different for each of the clinical conditions.

In Step S25, the neighboring pixel pattern generating unit 160 generates neighboring pixels (neighboring pixel pattern) to be used in predicting a pixel value. Step S25 can be implemented by performing a similar process to Step S15.

In Step S26, the pixel value prediction unit 190 predicts a pixel value of a pixel which is a target for coding. To be more specific, the pixel value prediction unit 190 obtains, from the prediction knowledge database 180, an appearance distribution of a pixel value corresponding to the clinical condition obtained in Step S22 and the neighboring pixel pattern generated in Step S15. The obtained frequency distribution indicates the actual pixel values often taken when the clinical condition and the neighboring pixels are equivalent, and the pixel value prediction unit 190 calculates the prediction probability of the pixel value according to the appearance distribution. Expression 1 is used in calculating the prediction probability of the pixel value. In Expression 1, P(i) indicates the probability of the pixel value of the prediction target pixel being i, $C_k$ indicates the value stored Kth of the appearance distribution in the prediction knowledge database 180 (the value indicating how many times the pixel value k has appeared), and N indicates the largest possible pixel value.

[Math. 1]

$$P(i) = \frac{C_i}{\sum_{k=0}^{N} C_k}$$ Expression 1

Figures 25, 26:
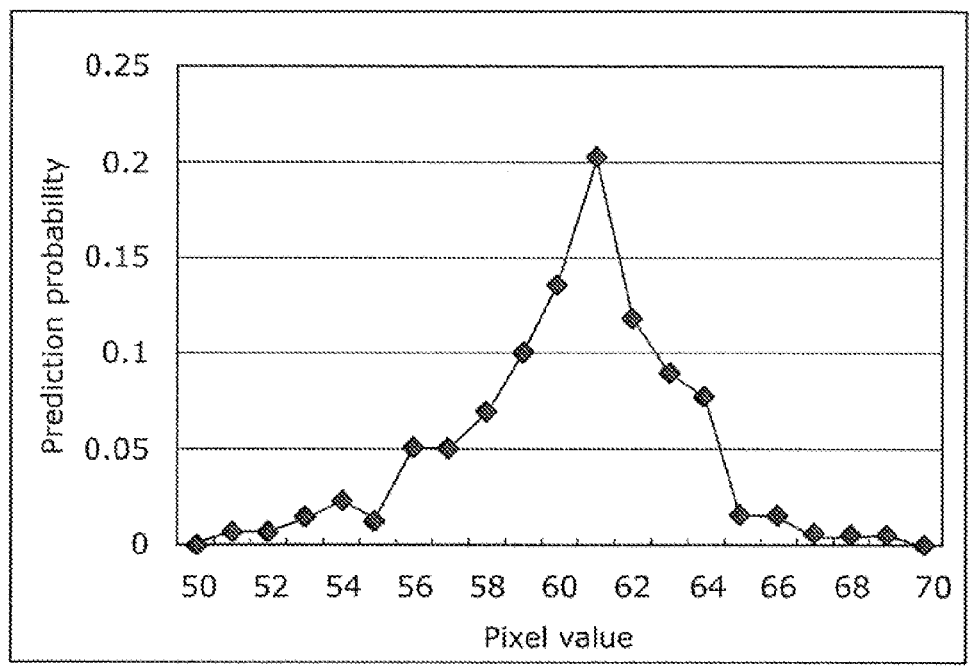
FIG. 25 is a diagram illustrating an example of prediction probability when a pixel value is predicted using a knowledge database, according to Embodiment 1.
FIG. 26 is a diagram for explaining a method of coding based on the prediction probability of a pixel value, using Huffman coding, according to Embodiment 1.

FIG. 25 is a diagram illustrating an example of the prediction probability when a pixel value is predicted using information in the prediction knowledge database 180. FIG. 25 indicates the prediction probability only in the range of the pixel values between 50 and 70 inclusive. However, in practice, the prediction probability is calculated from the smallest value (0 in many cases) to the largest value (8 bit, 10 bit, 12 bit, and so on) for the pixel values to be used.

It is to be noted that, in the steps described above, it is assumed that the appearance distribution corresponding to the clinical condition and the neighboring pixel pattern of the prediction target pixel is always present in the prediction knowledge database 180. When the number of the case data items are sufficient (from several thousand cases to tens of thousand cases), it is possible to construct the prediction knowledge database 180 which can support all the cases.

It is to be noted that, processes for the case where a sufficient number of appearance distributions are not present in the prediction knowledge database 180 due to a lack of case data items or the like, in other words, for the case where the appearance distribution corresponding to the clinical condition and the neighboring pixel pattern is not sufficiently present will be described later.

In Step S27, the coding unit 200 actually performs coding based on the prediction performed in Step S26. As a method of coding, the arithmetic coding, Range Coder, or Huffman coding can be used. In the case of this exemplary embodiment, the most suitable coding method is the arithmetic coding or Range Coder. The sum of the prediction probability P(0) to P(N) of a pixel value is 1, For that reason, when the arithmetic coding or Range Coder is employed, it is possible to directly perform coding using the prediction probability of the pixel value. The arithmetic coding and Range Coder are superior to Huffman coding in terms of compression efficiency as well.

FIG. 26 is a diagram for explaining a method of coding based on the prediction probability of a pixel value, using Huffman coding. In order to represent the pixel value of 256 tones, an 8 bit code is necessary in general. In Huffman coding, however, the higher the prediction probability of the pixel value is, the shorter the code length of a code is assigned, and the higher the prediction probability of the code is, the longer the code length of a code is assigned. In this case, when the prediction is right, a pixel value can be represented by a code having a short code length, and as a result, it is possible to compress the data amount. In the example illustrated in FIG. 26, the pixel values 59 and 60 with the highest prediction probability are assigned with Huffman codes 00 and 01, respectively, with the shortest code length. With this, the code length can be rendered two bits with a probability of 1/2 (the prediction probability 0.25 of the pixel value 59+the prediction probability 0.25 of the pixel value 60), and thus it is possible to compress a medical image with high compression efficiency.

Above-described Steps S23, S24, S25, S26, and S27 are repeatedly performed on all the pixels (Step S28).

When the processes have been performed on all of the pixels, the procedure proceeds to Step S29. In Step S29, the output unit 210 outputs the coded data.

In this exemplary embodiment, compression on a text portion (diagnostic finding information) is not particularly described. This is because, when comparing an image and a text, the image has significantly a larger volume than the text, and thus the compression of the diagnostic finding information portion is not important that much. The text portion may be left uncompressed, or may be compressed using a compression method which is generally employed, such as ZIP, bzip2, prediction by partial matching (PPM). Since the diagnostic finding information of a medical image often has a regularity to some extent in the style of the writing, a high compression efficiency can be expected even with a general compression method. Furthermore, since the words used in the diagnostic finding information of a medical image is limited in many cases, use of a dictionary in which medical terms are stored in advance is effective for compression as well.

As described above, according to Embodiment 1, diagnostic finding information is utilized for figuring out the clinical condition and the clinical condition range information. In addition, a pattern (neighboring pixel pattern) of pixel values in a neighboring pixel region which is used for predicting a pixel value from an image on which frequency analysis has been performed is generated. Furthermore, by performing prediction of a pixel value of a prediction target pixel with use of, as knowledge, an appearance distribution of an actual pixel value which corresponds to the clinical condition obtained from a past case and the neighboring pixel pattern, it is possible to predict a pixel value suitable to an image (a medical image, in this case) of a target for compression. For that reason, it is possible to compress a medical image with high compression efficiency and a lossless scheme.

In addition, the neighboring pixel pattern is generated by performing threshold processing. A pixel having a large pixel value in an image on which frequency analysis has been performed is a pixel having a large amount of information. For that reason, it is possible to generate a neighboring pixel pattern of pixels having a large amount of information. With this, it is possible to predict a pixel value of a prediction target pixel with accuracy.

Embodiment 2

In this exemplary embodiment, a method of automatically determining a threshold for used in generating a neighboring pixel pattern, and a method of holding the threshold for each clinical condition will be described. The basic configuration is the same as the basic configuration described in Embodiment 1, and thus only the operation of determining a threshold will be described below.

[Automatic Adjustment of a Threshold]

In Embodiment 1, a predetermined value is used as a threshold.

When the threshold is inappropriately set, there is a problematic possibility that a suitable neighboring pixel pattern cannot be generated because a region which is supposed to be used for prediction is overlooked, or to the contrary, a region which is unnecessary for prediction is included in a region to be used. This can be solved by automatically determining the threshold. To be more specific, first, the cases included in the case database 220 are separated into cases for study and cases for evaluation, Evaluation is performed by cross validation while the value of the threshold is changed, and a threshold with the highest evaluation (here, the compression efficiency for the cases for evaluation) is employed, thereby obtaining a suitable threshold in advance.

With this method, the process of obtaining a suitable threshold is added when constructing the prediction knowledge database 180. Although time is taken in constructing the prediction knowledge database 180, the addition does not affect the rate of actual compression, and thus it is suitable for practical use.

[Use of a Threshold for Each Clinical Condition]

It is also possible to use a different threshold for each clinical condition. A different threshold is used for each clinical condition because, since the complexity of the texture significantly differs for each clinical condition, there is a possibility that a neighboring pixel pattern which is suitable to all of the clinical conditions cannot be generated with a common threshold. The threshold for each clinical condition may be determined manually in advance. In addition, the threshold may be determined automatically by (i) separating the cases included in the case database 220 into the cases for study and the cases for evaluation, (ii) performing evaluation by cross validation while the value of the threshold is changed, and (iii) employing the threshold with the highest evaluation (here, the compression efficiency for the cases for evaluation).

When the threshold for each clinical condition is used, it is necessary to hold the thresholds in the prediction knowledge database 180. To be more specific, a table in which the threshold for each clinical condition is stored as illustrated in FIG. 27 is held in addition to the table in which the appearance distribution is held as illustrated in FIG. 18. The threshold obtaining unit 170 obtains, from the prediction knowledge database 180, a corresponding threshold using the clinical condition as a key, and the neighboring pixel pattern generating unit 160 generates a neighboring pixel pattern using the threshold obtained by the threshold obtaining unit 170. By employing the threshold suitable to the clinical condition as described above, it is possible to generate a neighboring pixel pattern reflecting the complexity or characteristics of the texture according to the clinical condition. This allows prediction with higher accuracy, and as a result, it is possible to improve the compression efficiency.

It is to be noted that, it is also possible to set a threshold for each time phase other than the clinical condition. Use of the threshold for each time phase makes it possible to improve, the compression efficiency of clinical conditions each having different complexity of the texture according to the time phase.

According to Embodiment 2 as described above, by employing the threshold suitable to the clinical condition, it is possible to generate a neighboring pixel pattern reflecting the complexity or characteristics of the texture according to the clinical condition. This allows prediction with higher accuracy, and as a result, it is possible to improve the compression efficiency.

Embodiment 3

In Embodiment 1, the prediction knowledge database 180 for predicting a pixel value is created using the case database 220 in which past cases are stored. When a sufficient number of cases are present in the case database 220, it is possible to create the ideal prediction knowledge database 180 without shortage. However, when there is a shortage of cases stored in the case database 220 and a sufficient frequency distribution cannot be created, the appearance distribution necessary for prediction might not be present in the prediction knowledge database 180. In this exemplary embodiment, a method for dealing with such a case will be described. It is to be noted that, also in this exemplary embodiment, the basic configuration is the same as the basic configuration described in Embodiment 1, and thus the following describes only the operations of the pixel value prediction unit 190 and the neighboring pixel pattern generating unit 160.

[A Measure when Data which Matches a Clinical Condition and a Neighboring Pixel Pattern of the Prediction Target Pixel are not Present in the Prediction Knowledge Database]

Figure 28:
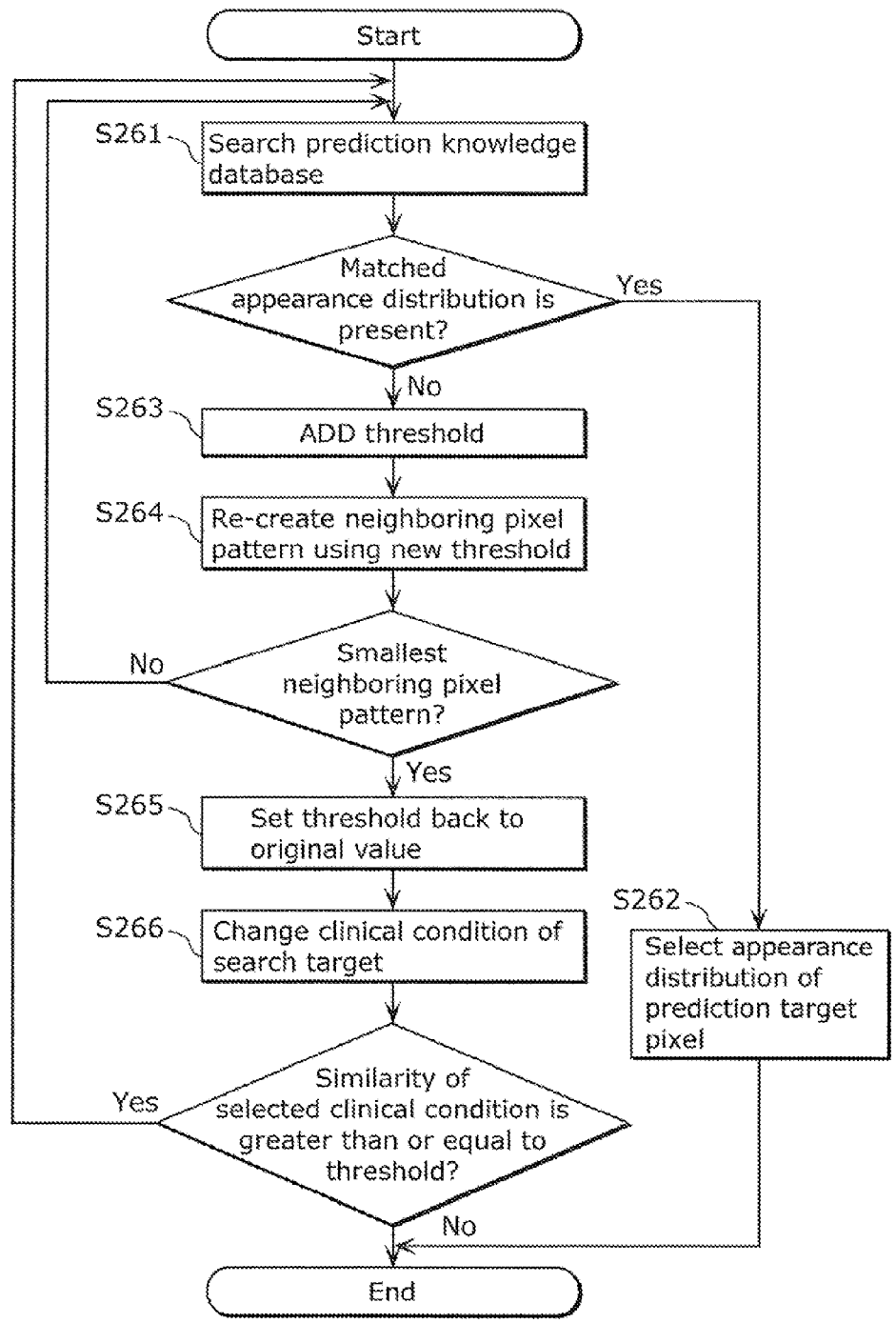
FIG. 28 is a diagram illustrating a flowchart of prediction knowledge database referring processing according to Embodiment 3.

FIG. 28 illustrates the flow of operations for obtaining an appearance distribution from the prediction knowledge database 180 according to this exemplary embodiment. This processing is performed within the prediction process (Step S26) of the pixel value illustrated in the flowchart of medical image compression in FIG. 24. The following describes in detail.

In Step S261, the pixel value prediction unit 190 examines whether or not row data which includes the clinical condition of a prediction target pixel and the appearance distribution corresponding to the neighboring pixel pattern is present in the prediction knowledge database 180. As a result, when perfectly-matched row data is present in the prediction knowledge database 180, the pixel value prediction unit 190 obtains the appearance distribution in Step S262 and ends the processing.

When a matched frequency distribution is not present, the neighboring pixel pattern generating unit 160 adds an arbitrary positive value to the threshold in Step S263, and re-creates a neighboring pixel pattern with use of a new threshold in Step S264.

The purpose of this process is to generate a neighboring pixel pattern having a narrow range by setting the threshold high. This is because, even when a corresponding frequency distribution is not present in the prediction knowledge database 180 with a neighboring pixel pattern having a broad range, the possibility that the corresponding frequency distribution can be obtained increases by re-setting the neighboring pixel pattern to be narrow. On that basis, the procedure goes back to Step S261, and the pixel value prediction unit 190 refers to the prediction knowledge database 180 using the clinical condition and the newly created neighboring pixel pattern as keys. It is to be noted that, when the neighboring pixel pattern created in Step S 264 has the smallest size (1×1), the procedure proceeds to the next step. It is determined, by this step, that the appearance distribution which matches the clinical condition of the prediction target pixel cannot be obtained.

In the subsequent steps, a process of extending the range of the clinical conditions to be examined will be performed.

In Step S265, the neighboring pixel pattern generating unit 160 sets the threshold back to the original value, and generates a neighboring pixel pattern based on the reset threshold.

In Step S266, the pixel value prediction unit 190 examines, as a new target, a clinical condition indicating a pixel value distribution similar to the pixel value distribution of the clinical condition of the prediction target pixel. This is because, even when the clinical conditions are different, when a clinical condition indicating a similar frequency distribution is present, it is possible to perform prediction with high accuracy by substituting the appearance distribution. Here, as the similarity between the clinical conditions, for example, the degree of overlap of the appearance distributions can be obtained and used based on the Bhattacharyya distance indicated in Expression 2. The Bhattacharyya distance is suitable to obtain the degree of overlap of the appearance distributions, and the similarity of clinical conditions is regarded as being higher as the Bhattacharyya distance is closer to 1.0.

When the similarity of selected clinical conditions is higher than or equal to the threshold, two clinical conditions are regarded as being similar to each other, and the procedure goes back to Step S261, and the processes subsequent to Step S 261 are repeatedly performed using the appearance distribution of the clinical condition similar to the clinical condition of the prediction target pixel. It is to be noted that, when two or more similar clinical conditions are present, the clinical conditions are sequentially selected from the clinical condition having the largest Bhattacharyya distance, and processes subsequent to Step S261 are repeatedly performed. When the similarity is lower than the threshold, prediction based on the similar clinical condition becomes difficult, and thus obtaining the appearance distribution from the prediction knowledge database 180 is given up. It is to be noted that, the threshold here may be set to a proper value manually, or may be determined experimentally. With the steps as described above, the possibility of obtaining an appearance distribution is increased significantly, compared to the case where the prediction knowledge database 180 is referred to simply using the clinical condition and the neighboring pixel pattern as keys.

[Math. 2]

$$d(A, B) = \sum_{i \in C} \sqrt{h_A(i) h_B(i)} \quad \text{Expression 2}$$

Here, d(A, B) indicates the Bhattacharyya distance between the appearance distribution A and the appearance distribution B. C indicates the set of the pixel values, $h_A(i)$ indicates the number of appearance of the pixel value i in the appearance distribution A, and $h_B(i)$ indicates the number of appearance of the pixel value i in the appearance distribution B.

It is to be noted that, when the appearance distribution cannot be obtained at the end, it is impossible to predict the pixel value using the prediction knowledge database 180, and thus the pixel value is predicted using the conventionally and generally used technique in which the pixel value is predicted from the pixel value of a neighboring pixel using a mathematical expression. As a method of prediction, the plane prediction method, the Paeth method, the Loco-I method, and so on are available. The Paeth method and the Loco-I method are prediction methods of a pixel value used in PNG and JPEG-LS, respectively. With these prediction methods, a pixel value of the target pixel is simply predicted only from a pixel value of an adjacent pixel, and thus, although the prediction accuracy is lower than the prediction accuracy of the case where the appearance distribution of the prediction knowledge database 180 is used, previous knowledge is not required.

[When an Actual Pixel Value is not Included in the Pixel Value Frequency Distribution]

Even when the appearance distribution can be obtained through the steps described above, the number of appearance of an actual pixel value in the appearance distribution might be 0 in some cases. In such a case, the prediction probability is 0 for the pixel value with the number of appearance being 0, and coding might be impossible with some coding method.

The simplest solution for this problem is to initialize the smallest value of each pixel in the appearance distribution to be 1. This case is problematic in that there is a possibility that the prediction probability of a pixel which is supposed to have 0 appearance is calculated to be wrongly high.

In this exemplary embodiment, a measure described below is taken in order to solve the above-described problem. Specifically, Expression 3 is used in calculating the prediction probability of each pixel value. In Expression 3, P(i) indicates the prediction probability of the pixel i, $C_k$ indicates the value stored Kth of the appearance distribution in the prediction knowledge database 180 (the value indicating how many times the pixel value k has appeared), and N indicates the largest possible pixel value. In addition, a in the Expression is an arbitrary constant number which is larger than 0 and smaller than 1. Furthermore, M in the Expression is a positive constant number. This Expression means that a probability for representing a pixel which is not present in an appearance distribution is prepared in advance, and a pixel with a value of 0 in the appearance distribution is allowed to be expressed with use of the probability. It is to be noted that as to a pixel with a nonzero value in the appearance distribution, the prediction probability of a pixel value is calculate as with Expression 1.

[Math. 3]

$$P(i) = \begin{cases} (1-a) \times \dfrac{C_i}{\sum_{k=0}^{N} C_k} & (C_i \neq 0) \\ a \times \dfrac{1}{M} & (C_i = 0) \end{cases} \quad \text{Expression 3}$$

In addition, used of Expression 4 makes it possible to dynamically change the probability a which is to be assigned to a pixel value that is not present in the appearance distribution in Expression 3. Here, $c_n$ indicates the number of times that the number of appearance of the prediction target pixel is one or more, and $f_n$ indicates the number of times that the number of appearance of the prediction target pixel is 0, in the prediction of a pixel value for the past n times. In addition, the constant number A indicates the largest probability to be assigned to a pixel with the number of appearance of 0. Here, A is an arbitrary constant number which is larger than 0 and smaller than 1. Such expressions are used for utilizing the characteristics of an image, that is, a prediction is highly likely right where predictions have been right continuously, and highly likely wrong where predictions have been wrong continuously. It is to be noted that, when there are two or more pixels with the number of appearance being 0, the prediction probability of all of the pixel values may be the same, or a pixel having a pixel value close to an average value of the appearance distribution may be given a large weight.

[Math. 4]

$$a = A \times \dfrac{f_n}{(c_n + f_n)} \quad \text{Expression 4}$$

With the processes described above, it is possible to perform coding while maintaining a high coding efficiency, even when perfectly-matched knowledge cannot be obtained from the prediction knowledge database 180.

According to Embodiment 3 described above, it is possible to generate a neighboring pixel pattern having a range narrower than a current range, by updating a threshold to have a value larger than a current value when the appearance distribution cannot be obtained. For that reason, even when a corresponding frequency distribution is not present in the prediction knowledge database with a neighboring pixel pattern having a broad range, the possibility that the corresponding frequency distribution can be obtained increases by resetting the neighboring pixel pattern to be narrow.

In addition, even when an appearance distribution is not present in the prediction knowledge database after changing the neighboring pixel pattern, it is possible to predict a pixel value using the appearance distribution created for a different clinical condition.

Furthermore, it is possible to set the prediction probability of all of the pixel values to be a value larger than 0. For that reason, it is possible to perform coding even when a coding method with which a pixel value having a prediction probability of 0 cannot be coded is employed.

It is to be noted that the medical image compression device according to the above-described Embodiments 1 to 3 may be implemented by a computer.

Figure 29:
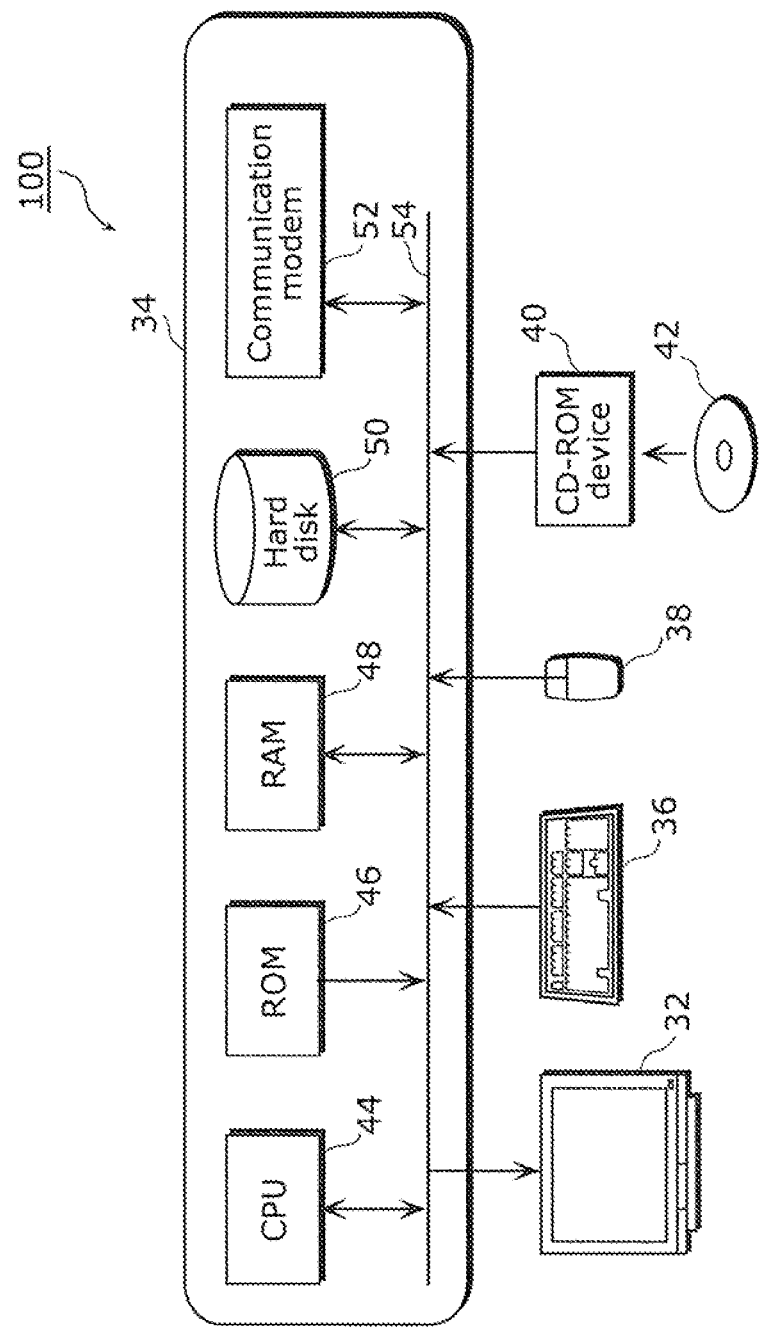
FIG. 29 is a block diagram illustrating a hardware configuration of a computer system implementing the medical image compression device.

FIG. 29 is a block diagram illustrating a hardware configuration of a computer system implementing the medical image compression device.

The medical image compression device includes: a computer 34; a keyboard 36 and a mouse 38 which are used for providing an instruction to the computer 34; a display 32 for presenting information such as a result of operation performed by the computer 34; a compact disc-read only memory (CD-ROM) device 40 for reading a program to be executed by the computer 34; and a communication modem (not illustrated).

The program which is a process performed by the medical image compression device is stored in the CD-ROM 42 that is a computer-readable recording medium, and read by the CD-ROM device 40. Alternatively, the program is read by the communication modem 52 via the computer network.

The computer 34 includes: a central processing unit (CPU) 44; a read only memory (ROM) 46; a random access memory (RAM) 48; a hard disk 50; a communication modem 52; and a bus 54.

The CPU 44 executes the program read via the CD-ROM device 40 or the communication modem 52. The ROM 46 stores a program or data necessary for the operation of the computer 34. The RAM 48 stores data such as a parameter at the time of executing the program. The hard disk 50 stores a program or data. The communication modem 52 communicates with other computers via the computer network. The bus 54 interconnects the CPU 44, the ROM 46, the RAM 48, the hard disk 50, the communication modem 52, the display 32; the keyboard 36; the mouse 38; and the CD-ROM device 40.

It is to be noted that the prediction knowledge database creation device according to the above-described Embodiments 1 to 3 may be implemented by a computer as with the medical image compression device.

In addition, the components that constitute each of the above devices may be partly or wholly realized by one system LSI (Large Scale Integration). The system LSI is an ultra-multifunctional LSI produced by integrating a plurality of components on one chip, and is actually a computer system that includes a microprocessor, a ROM, a RAM, and the like. A computer program is stored on the RAM. Functions of each of the system LSI can be achieved by the microprocessor operating in accordance with the computer program.

Further, in addition, a part or all of the constituent elements included in the respective devices may be configured as an IC card which can be attached and detached from the respective devices or as a stand-alone module. The IC card or the module is a computer system configured from a microprocessor, a ROM, a RAM, and so on. The IC card or the module may also include the aforementioned super-multi-function LSI. The IC card or the module achieves its function through the microprocessor's operation according to the computer program. The IC card or the module may also be implemented to be tamper-resistant.

In addition, the present disclosure may be a method described above. In addition, these methods may be implemented as a computer program, using a computer, and may also be a digital signal including the computer program.

More specifically, the computer program causes a computer to execute a medical image compression method, including: obtaining a target image which is a medical image to be compressed and diagnostic finding information for the target image; dividing the target image into regions each corresponding to a different one of clinical conditions based on the diagnostic finding information; for an arbitrary pixel, referring to a prediction knowledge database in which an appearance distribution of a pixel value of an arbitrary pixel is stored for each of the clinical conditions, and calculating a prediction probability of a pixel value of a prediction target pixel based on the clinical condition of the prediction target pixel and the appearance distribution of the pixel value of the prediction target pixel, the appearance distribution of the pixel value of the arbitrary pixel corresponding to a pixel value included in a predetermined neighboring range; coding the pixel value of the prediction target pixel based on the prediction probability of the pixel value calculated in the referring; and outputting a code of the prediction target pixel after being coded in the coding.

Such computer programs or digital signals according to the present disclosure may be recorded on computer-readable non-volatile recording media such as flexible discs, hard disks, CD-ROMs, MOs, DVDs, DVD-ROMs, DVD-RAMs, BDs (Blu-ray Disc (registered trademark)), and semiconductor memories. In addition, the present disclosure may also be realized by a digital signal recorded on these non-volatile recording media.

Furthermore, the present disclosure may also be realized by the transmission of the aforementioned computer program or digital signal via a telecommunication line, a wireless or wired communication line, a network represented by the Internet, a data broadcast and so on.

The apparatuses (or computers or a computer system) according to the present disclosure may also be implemented as a computer system including a microprocessor and a memory, in which the memory stores the aforementioned computer program and the microprocessor operates according to the computer program.

Furthermore, it is also possible to execute another independent computer system by transmitting the programs or the digital signals recorded on the aforementioned non-transitory recording media, or by transmitting the programs or digital signals via the aforementioned network and the like.

Figure 30:
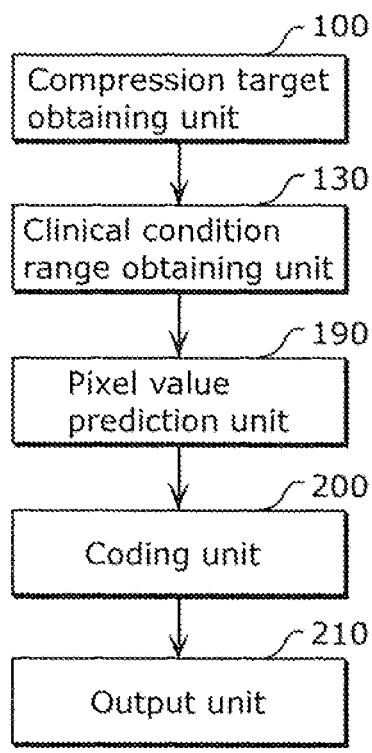
FIG. 30 is a diagram illustrating indispensable structural elements of the medical image compression device according to one or more exemplary embodiments.

FIG. 30 illustrates indispensable structural elements of the medical image compression device according to the present disclosure, among the structural elements of the medical image compression device illustrated in FIG. 1. The indispensable structural elements include: the compression target obtaining unit 100; the clinical condition range obtaining unit 130; the pixel value prediction unit 190; the coding unit 200; and the output unit 210. It is preferable that the other structural elements are also included, however, they need not necessarily be included.

The medical image compression device and the prediction knowledge database creation device according to one or more aspects have been described based on the embodiments, however, the present disclosure is not limited to these embodiments. Those skilled in the art will readily appreciate that various modifications may be made in the exemplary embodiment, and other embodiments may be made by arbitrarily combining some of the structural elements of different exemplary embodiments without materially departing from the principles and spirit of the inventive concept, the scope of which is defined in the appended Claims and their equivalents.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the medical image compression device and the prediction knowledge database creation device apparatus according to each of the embodiments is a program described below.

The program causes a computer to execute the medical image compression method which includes: obtaining a target image which is a medical image to be compressed and diagnostic finding information for the target image; dividing the target image into regions each corresponding to a different one of clinical conditions based on the diagnostic finding information; for an arbitrary pixel, referring to a prediction knowledge database in which an appearance distribution of a pixel value of an arbitrary pixel is stored for each of the clinical conditions, and calculating a prediction probability of a pixel value of a prediction target pixel based on the clinical condition of the prediction target pixel and the appearance distribution of the pixel value of the prediction target pixel, the appearance distribution of the pixel value of the arbitrary pixel corresponding to a pixel value included in a predetermined neighboring range; coding the pixel value of the prediction target pixel based on the prediction probability of the pixel value calculated in the referring; and outputting a code of the prediction target pixel after being coded in the coding.

The herein disclosed subject matter is to be considered descriptive and illustrative only, and the appended Claims are of a scope intended to cover and encompass not only the particular embodiments disclosed, but also equivalent structures, methods, and/or uses.

INDUSTRIAL APPLICABILITY

The present disclosure is applicable to a medial image compression device, and so on, which compress a medical image. In addition, other than a medical image, the present disclosure can also be applied to compression of an image of data in which an image and a description text are included as a set (a pictorial book, for example).

The invention claimed is:

1. A medical image compression device comprising:
a compression target obtaining unit configured to obtain (i) a target image which is a medical image to be compressed and (ii) diagnostic finding information for the target image;
a clinical condition range obtaining unit configured to divide the target image into regions each corresponding to a different one of clinical conditions based on the diagnostic finding information;
a pixel value prediction unit configured to, for an arbitrary pixel, refer to a prediction knowledge database in which an appearance distribution of a pixel value of an arbitrary pixel is stored for each of the clinical conditions, and calculate a prediction probability of a pixel value of a prediction target pixel based on the clinical condition of the prediction target pixel and the appearance distribution of the pixel value of the prediction target pixel, the appearance distribution of the pixel value of the arbitrary pixel corresponding to a pixel value included in a predetermined neighboring range;
a coding unit configured to code the pixel value of the prediction target pixel based on the prediction probability of the pixel value calculated by the pixel value prediction unit; and
an output unit configured to output a code of the prediction target pixel after being coded by the coding unit.

2. The medical image compression device according to claim 1,
wherein the diagnostic finding information includes at least information related to the clinical condition and a position of the clinical condition, as a result of an examination for diagnosis of the target image by a doctor,
the medical image compression device further comprises:
a finding analyzing unit configured to refer to a medical dictionary in which (i) a clinical condition keyword which is a term indicating a clinical condition and (ii) a position keyword which is a term indicating a position of the clinical condition are held, and extract the clinical condition keyword and the position keyword from the diagnostic finding information obtained by the compression target obtaining unit;
an image frequency analyzing unit configured to perform frequency analysis on the target image obtained by the compression target obtaining unit; and
a neighboring pixel pattern generating unit configured to generate, in the target image, a neighboring pixel pattern including pixel values of pixels included in a predetermined range which includes neighboring pixels of the prediction target pixel, the target image being the target image on which the frequency analysis has been performed by the image frequency analyzing unit,
the clinical condition range obtaining unit is configured to refer to an anatomical structure database in which the position keyword and range information of a clinical condition on a medical image are held in association with each other, and obtain range information of a clinical condition on the target image which is obtained by the compression target obtaining unit, the range information of the clinical condition on the target image corresponding to the position keyword extracted by the finding analyzing unit,
the prediction knowledge database holds a plurality of items of row data including (i) the clinical condition keyword, (ii) the pixel values of pixels included in the predetermined range which includes the neighboring pixels of an arbitrary pixel, and (iii) the appearance distribution of the pixel value of the arbitrary pixel, and
the pixel value prediction unit is configured to refer to the prediction knowledge database to obtain the row data including the clinical condition keyword extracted by the finding analyzing unit and the neighboring pixel pattern generated by the neighboring pixel pattern generating unit, and calculate a prediction probability of the pixel value of the prediction target pixel based on the appearance distribution of the pixel value of the arbitrary pixel included in the obtained row data.

3. The medical image compression device according to claim 2,
wherein the neighboring pixel pattern generating unit is configured to generate, as the neighboring pixel pattern, a pattern including a pixel value larger than or equal to a threshold, among pixel values of a pixel included in the predetermined range which includes the neighboring pixels of the prediction target pixel, in the target image on which the frequency analysis has been performed by the image frequency analyzing unit.

4. The medical image compression device according to claim 3,
wherein the neighboring pixel pattern generating unit is configured to generate, as the neighboring pixel pattern, a pattern which includes a pixel value larger than or equal to the threshold corresponding to the clinical condition keyword extracted by the finding analyzing unit, among the pixel values of the pixels included in the predetermined range which includes the neighboring pixels of the prediction target pixel, in the target image on which the frequency analysis has been performed by the image frequency analyzing unit.

5. The medical image compression device according to claim 3,
wherein when the pixel value prediction unit cannot obtain the row data,
the neighboring pixel pattern generating unit is further configured to update the threshold to a value larger than a current value, and generate the neighboring pixel pattern using the threshold resulting from the update.

6. The medical image compression device according to claim 5,
wherein when the pixel value prediction unit cannot obtain the row data even when the threshold resulting from the update is used, the pixel value prediction unit is further configured to refer to the prediction knowledge database to obtain row data including (i) a clinical condition keyword different from the clinical condition keyword extracted by the finding analyzing unit and (ii) the neighboring pixel pattern generated by the neighboring pixel pattern generating unit, and calculate a prediction probability of the pixel value of the prediction target pixel, based on the appearance distribution of the pixel value of the arbitrary pixel included in the obtained row data.

7. The medical image compression device according to claim 2,
wherein when the number of appearance of the pixel value of the arbitrary pixel is 0, the pixel value prediction unit is configured to calculate a predetermined value larger than 0 as the prediction probability of the pixel value of the prediction target pixel.

8. The medical image compression device according to claim 7,
wherein the pixel value prediction unit is configured to dynamically change the predetermined value larger than 0, according to a sporadic rate of the arbitrary pixel having a pixel value with a number of appearance of 0 in a latest process which is performed for a predetermined number of times.

9. A medical image compression method, comprising:
obtaining a target image which is a medical image to be compressed and diagnostic finding information for the target image; dividing the target image into regions each corresponding to a different one of clinical conditions based on the diagnostic finding information;
for an arbitrary pixel, referring to a prediction knowledge database in which an appearance distribution of a pixel value of an arbitrary pixel is stored for each of the clinical conditions, and calculating a prediction probability of a pixel value of a prediction target pixel based on the clinical condition of the prediction target pixel and the appearance distribution of the pixel value of the prediction target pixel, the appearance distribution of the pixel value of the arbitrary pixel corresponding to a pixel value included in a predetermined neighboring range;
coding the pixel value of the prediction target pixel based on the prediction probability of the pixel value calculated in the referring; and
outputting a code of the prediction target pixel after being coded in the coding.

10. A non-transitory computer-readable recording medium for use in a computer, the recording medium having a computer program recorded thereon for causing the computer to execute: the medical image compression method according to claim 9.

11. A prediction knowledge database creation device which creates a prediction knowledge database for use in the medical image compression device according to claim 1, the prediction knowledge database creation device comprising:
a case selecting unit configured to select a nonselected case from a case database as a result of an examination for diagnosis of the medical image by a doctor, the case database holding a plurality of cases each including a medical image and diagnostic finding information which includes at least a clinical condition and information related to a position of the clinical condition;
a finding analyzing unit configured to refer to a medical dictionary in which (i) a clinical condition keyword which is a term indicating a clinical condition and (ii) a position keyword which is a term indicating a position of the clinical condition are held, and extract the clinical condition keyword and the position keyword from the diagnostic finding information included in the case selected by the case selecting unit;
the clinical condition range obtaining unit configured to refer to an anatomical structure database in which the position keyword and range information of a clinical condition on a medical image are held in association with each other, and obtain range information of a clinical condition on the medical image, which corresponds to the position keyword extracted by the finding analyzing unit and included in the case selected by the case selecting unit;
an image frequency analyzing unit configured to perform frequency analysis on the medical image included in the case selected by the case selecting unit;
a neighboring pixel pattern generating unit configured to generate a neighboring pixel pattern including pixel values of pixels included in a predetermined range which includes neighboring pixels of a target pixel, in the medical image on which the frequency analysis has been performed by the image frequency analyzing unit, and
a pixel value frequency distribution updating unit configured to obtain, from the prediction knowledge database, row data corresponding to the clinical condition keyword extracted by the finding analyzing unit and the neighboring pixel pattern generated by the neighboring pixel pattern generating unit, and update, using the pixel value of the target pixel, an appearance distribution of a pixel value of an arbitrary pixel included in the obtained row data.

* * * * *